(12) United States Patent
Tropsha et al.

(10) Patent No.: US 7,984,717 B2
(45) Date of Patent: Jul. 26, 2011

(54) DEVICES FOR AUGMENTATION OF LUMEN WALLS

(75) Inventors: Yelena G. Tropsha, Plymouth, MN (US); Warren L. Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1664 days.

(21) Appl. No.: 11/118,628

(22) Filed: Apr. 29, 2005

(65) Prior Publication Data

US 2006/0257446 A1    Nov. 16, 2006

(51) Int. Cl.
*A61B 19/00* (2006.01)
(52) U.S. Cl. ....................................................... 128/897
(58) Field of Classification Search ............. 600/29–32, 600/37; 128/897–899; 604/19, 27, 30–34; 424/183.1, 236.1, 239.1, 247.1, 423, 484
See application file for complete search history.

(56) References Cited

U.S. PATENT DOCUMENTS

| | | | |
|---|---|---|---|
| 4,059,684 A | 11/1977 | Gross et al. | |
| 4,331,783 A | 5/1982 | Stoy | |
| 4,337,327 A | 6/1982 | Stoy | |
| 4,369,294 A | 1/1983 | Stoy | |
| 4,370,451 A | 1/1983 | Stoy | |
| 4,379,874 A | 4/1983 | Stoy | |
| 4,420,589 A | 12/1983 | Stoy | |
| 4,631,188 A | 12/1986 | Stoy et al. | |
| 4,803,075 A | 2/1989 | Wallace et al. | |
| 5,007,940 A | 4/1991 | Berg | |
| 5,116,387 A | 5/1992 | Berg | |
| 5,158,573 A | 10/1992 | Berg | |
| 5,336,263 A * | 8/1994 | Ersek et al. .................... 424/422 |
| 5,451,406 A | 9/1995 | Lawin et al. | |
| 5,667,778 A | 9/1997 | Atala | |
| 5,755,658 A | 5/1998 | Wallace et al. | |
| 5,785,642 A | 7/1998 | Wallace et al. | |
| 5,879,697 A | 3/1999 | Ding et al. | |
| 6,042,875 A | 3/2000 | Ding et al. | |
| 6,098,629 A * | 8/2000 | Johnson et al. ................ 128/897 |
| 6,251,063 B1 | 6/2001 | Silverman et al. | |
| 6,251,064 B1 * | 6/2001 | Silverman et al. ............. 600/29 |
| 6,316,018 B1 | 11/2001 | Ding et al. | |
| 6,338,345 B1 | 1/2002 | Johnson et al. | |
| 6,358,197 B1 | 3/2002 | Silverman et al. | |
| 6,401,718 B1 | 6/2002 | Johnson et al. | |
| 6,423,332 B1 * | 7/2002 | Huxel et al. .................... 424/422 |
| 6,591,838 B2 | 7/2003 | Durgin | |
| 6,605,294 B2 | 8/2003 | Sawhney | |
| 6,652,883 B2 | 11/2003 | Goupil et al. | |
| 6,754,536 B2 | 6/2004 | Swoyer et al. | |

(Continued)

OTHER PUBLICATIONS

Walker et al., "Injectable Bioglass as a Potential Substitute for Injectable Polytetrafluroethylene Particles", *J. Urol.*, 148:645-7, 1992.

(Continued)

*Primary Examiner* — Samuel Gilbert
(74) *Attorney, Agent, or Firm* — Jeffrey J. Hohenshell; Michael J. Jaro

(57) ABSTRACT

A bulking device for implantation into a lumen wall that includes a bulking material that is configured to alter the portion of the lumen into which it is implanted and one or more therapeutic substances in association with the bulking material, wherein the device is configured to alter the portion of the lumen wall into which it is implanted. A method for inserting devices of the invention are also included.

10 Claims, 15 Drawing Sheets

U.S. PATENT DOCUMENTS

| | | | |
|---|---|---|---|
| 7,305,993 B2 | 12/2007 | Tropsha et al. | |
| 2002/0018812 A1* | 2/2002 | Busson et al. | 424/484 |
| 2002/0103424 A1 | 8/2002 | Swoyer et al. | |
| 2003/0099682 A1* | 5/2003 | Moussy et al. | 424/423 |
| 2004/0019388 A1* | 1/2004 | Starkebaum | 623/23.65 |
| 2004/0089313 A1* | 5/2004 | Utley et al. | 128/898 |
| 2005/0053642 A1* | 3/2005 | Ulbricht et al. | 424/443 |
| 2005/0096497 A1 | 5/2005 | Gerber et al. | |
| 2005/0187146 A1 | 8/2005 | Hemus et al. | |
| 2005/0245957 A1* | 11/2005 | Starkebaum et al. | 606/191 |
| 2005/0246037 A1 | 11/2005 | Starkebaum | |
| 2006/0074436 A1* | 4/2006 | Behl | 606/110 |
| 2006/0173472 A1 | 8/2006 | Starkebaum et al. | |
| 2006/0247768 A1 | 11/2006 | Starkebaum | |
| 2006/0257445 A1 | 11/2006 | Tropsha et al. | |
| 2006/0257446 A1 | 11/2006 | Tropsha et al. | |

OTHER PUBLICATIONS

Office Action mailed Jan. 27, 2009 for U.S. Appl. No. 11/118,614.
Office Action mailed Aug. 19, 2008 for U.S. Appl. No. 11/118,614.
Office Action mailed Dec. 24, 2008 for U.S. Appl. No. 11/118,620.

* cited by examiner

DEVICES FOR AUGMENTATION OF LUMEN WALLS

FIELD OF THE INVENTION

The invention relates generally to devices and methods for augmenting portions of lumen walls. More specifically, the invention relates to devices for augmenting lumen walls that include a therapeutic substance.

BACKGROUND OF THE INVENTION

There are a number of devices for implantation within the body of a patient to treat various conditions or disorders. A number of these devices are configured to be placed within a lumen wall. For example, U.S. Pat. No. 6,098,629 discloses a device for implantation within the esophagus to treat gastroesophageal reflux disease (GERD).

Implantation of any device within a patient can trigger the patient's autoimmune response and cause an inflammatory response, or an infection to occur. Devices such as those referred to above have an even greater risk of infection because of the location into which they are implanted, a lumen wall. Lumen walls are often non-sterile and therefore, the incidence of infection can be increased. Furthermore, implanted devices, such as those referred to above, are generally designed to only address the structural defects or concerns associated with a disease or condition.

Therefore, there remains a need for implantable devices that can treat the structural defects or concerns of a disease or condition as well as the underlying biochemical and chemical causes or effects, and still mitigate the possibility of infection or inflammatory response.

BRIEF SUMMARY OF THE INVENTION

One embodiment of the invention includes a bulking device, for implantation into a lumen wall, that includes a bulking material that is configured to alter the portion of the lumen into which it is implanted, and one or more therapeutic substances in association with the bulking material, wherein the device is configured to alter the portion of the lumen wall into which it is implanted. In one embodiment, the lumen wall that the device is to be implanted in is a sphincter, and in another embodiment it is some portion of the gastrointestinal wall not in the vicinity of a sphincter.

The invention also includes methods of altering at least a portion of a lumen wall that includes the steps of piercing the mucosa of the lumen wall to be altered, introducing a bulking material within the submucosa, wherein the bulking material is configured to alter a portion of the lumen wall into which it is implanted, and wherein the bulking material is associated with one or more therapeutic substances, and closing the mucosal opening.

The invention also includes a bulking device for implantation into a lumen wall that includes a swellable material that is configured to alter the portion of the lumen into which it is implanted, and at least one anti-inflammatory agent and at least one anti-infective agent in association with the swellable material, wherein the device is configured to alter the portion of the lumen wall into which it is implanted.

Another embodiment of the invention includes a bulking device for implantation in the esophagus in the vicinity of the lower esophageal sphincter, where the device includes a bulking material that is configured to alter the portion of the esophagus around the lower esophageal sphincter, and one or more therapeutic substances in association with the bulking material.

The invention also includes a method of augmenting a portion of the esophagus in the vicinity of the lower esophageal sphincter that includes the steps of piercing the mucosa of the esophagus to be augmente, introducing a bulking device within the submucosa, wherein the bulking material is configured to augment the portion of the esophagus into which it is implanted, and wherein the bulking material is associated with one or more therapeutic substances, and closing the mucosal opening.

Yet another embodiment of the invention includes a bulking device for implantation into a the esophagus to treat gastroesophageal disorder that includes a swellable material that is configured to alter the portion of the esophagus into which it is implanted, and at least one anti-inflammatory agent, at least one anti-infective agent, and at least one acid reduction agent in association with the swellable material, wherein the device is configured to alter the portion of the esophagus into which it is implanted.

A bulking device for implantation into the gastrointestinal tract for the treatment of obesity that includes a bulking material that is configured to alter the portion of the gastrointestinal tract into which it is implanted, and at least one anti-infective agent, and at least one anti-inflammatory agent in association with the bulking material

BRIEF DESCRIPTION OF THE DRAWINGS

FIG. 2b is a cross section of the lumen taken from the duodenum of FIG. 2a.

DETAILED DESCRIPTION OF THE INVENTION

Figure 1:
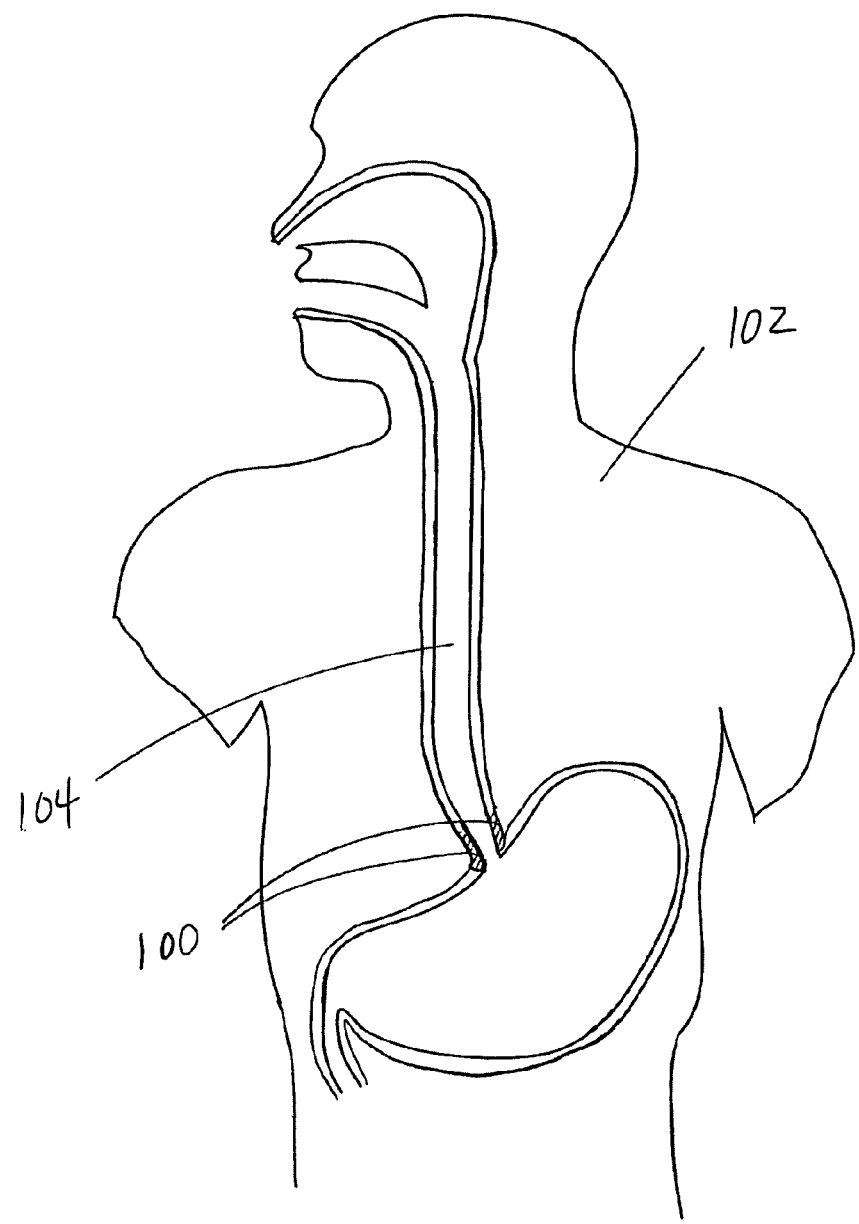
FIG. 1 shows a device of the invention implanted within a patient's esophagus, for example.

The invention includes a device, for implantation into a lumen wall, that has a bulking material that is configured to alter the portion of the lumen into which it is implanted, and one or more therapeutic substances in association with the bulking material. In one embodiment, the device is configured to alter the portion of the lumen wall into which it is implanted. FIG. 1 depicts a bulking device 100 of the invention placed with a patient 102. In this example, the bulking device 100 is placed within the wall of the esophagus 104.

Devices of the invention are generally configured for insertion into a lumen wall. Examples of lumen walls in which devices of the invention can be inserted include, but are not limited to the gastrointestinal tract wall, and the urinary tract wall. Specific areas in the gastrointestinal tract where the bulking devices of the invention can be implanted include, but are not limited to, the anal sphincter, the pylorus, the stomach, the esophagus, the lower esophageal sphincter, the upper esophageal sphincter, the duodenum, the small intestine, and the large intestine. In one embodiment a device of the invention is configured to be inserted into the wall of the gastrointestinal tract. For example, the device could be configured to be placed in the esophagus, the stomach, the duodenum, the large intestine, the small intestine, or the colon. In another embodiment a device of the invention could be configured to be inserted into the wall of the urinary tract. For example, within the urethra. Devices of the invention can be used to treat a number of conditions, including gut not limited to GERD, obesity, urinary incontinence, fecal incontinence, and gastroparesis.

In one embodiment, a device of the invention is configured to be inserted into the wall of a lumen in the vicinity of or around the vicinity of a sphincter. When a device of the invention is configured to be inserted in the vicinity of a sphincter, it is generally being inserted to augment the ability of the sphincter to close properly. When a sphincter is unable, due to disease or malformation, to close properly a number of conditions can be created. A device of the invention can be utilized to augment the sphincter, i.e. to allow the accompanying sphincter muscles to close it more effectively, or to increase the level of closure that the sphincter muscles can obtain. Examples of sphincters that can be augmented using devices of the invention include, but are not limited to the upper esophageal sphincter (UES), the lower esophageal sphincter (LES), the pyloric sphincter, the external or internal anal sphincters, and the urethral sphincter.

Another embodiment of the invention includes a device configured to augment a portion of the lumen wall not in the vicinity of or around the vicinity of a sphincter. For example, it may be desirable to implant a device of the invention within the stomach wall in order to treat obesity. Examples of structures that could be augmented in this fashion using a device of the invention include, but are not limited to the stomach, duodenum, small intestine, or some combination thereof.

Figure 2A:
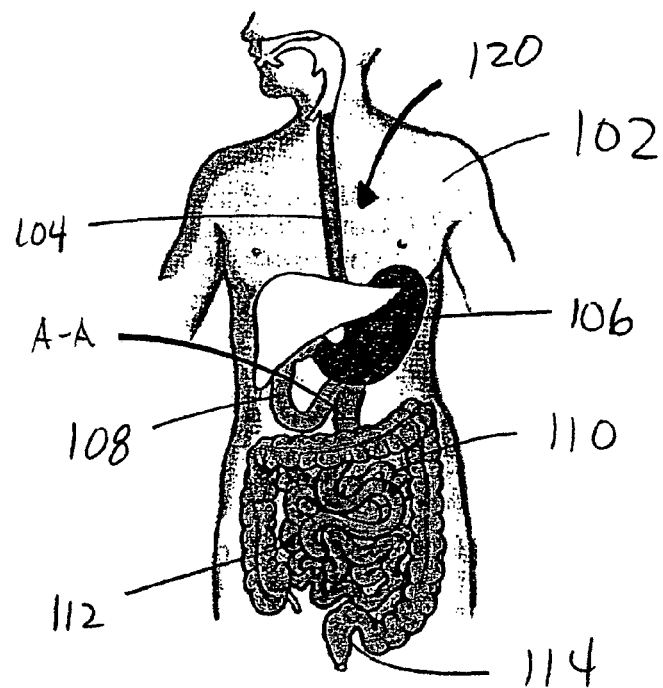
FIG. 2a depicts the gastrointestinal tract of a patient.
Figure 2B:
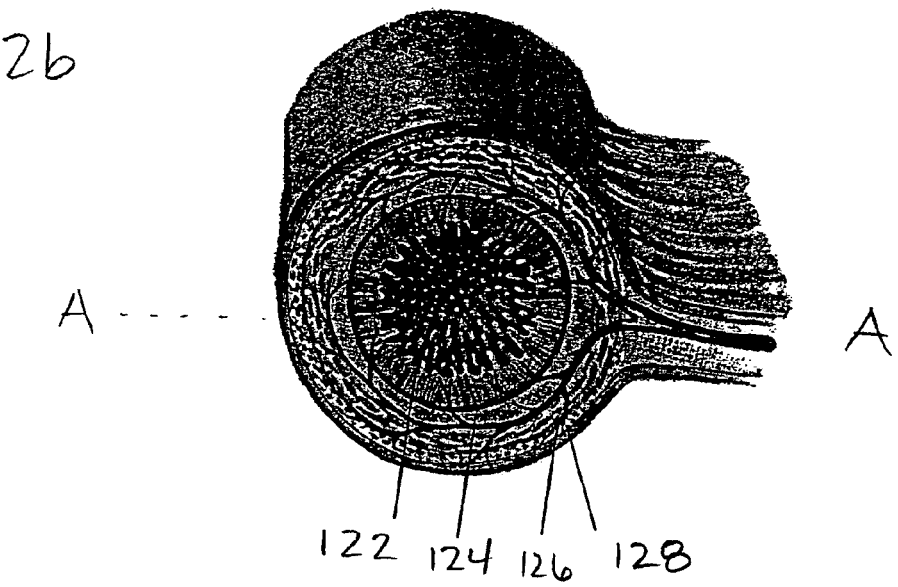

Devices of the invention are generally placed within a submucosal layer of the lumen wall. FIG. 2a depicts a portion of the gastrointestinal tract 120 of a patient 102. In this example, the esophagus 104, the stomach 106, the duodenum 108, the large intestine 110, the small intestine 112, and the colon 114 are depicted. As discussed above, a bulking device of the invention could be placed within the wall of any of these structures of the gastrointestinal tract 120. FIG. 2b depicts a cross section of a portion of the gastrointestinal tract 120, showing the mucosa 122, the submucosa 124, the muscularis 126, and the serosa 128. This portion could generally be depicting the gastrointestinal tract 120 at any portion along the structures depicted in FIG. 2a, but is specifically a cross section taken along line A-A in FIG. 2a of the duodenum 108. Devices of the invention are generally configured to be placed within the submucosa 124 of the lumen wall into which they are placed.

Bulking devices of the invention include a bulking material. Any material that can expand after implantation can accommodate the incorporation of a therapeutic substance can be utilized to make a bulking device in accordance with the invention. In one embodiment the bulking device is made of a material that is soft, compliant, and/or flexible, to minimize trauma within the lumen wall upon implantation. In one embodiment, the bulking material is compressed for implantation by a constraint or structure that forces it into a compressed size, and when that constraint or structure is released, it expands. In another embodiment of the invention, the bulking material expands upon absorption of a liquid, or is swellable.

One example of bulking materials that expand upon absorption of a liquid, or are swellable, are hydrogels. Examples of hydrogel materials that can be utilized as bulking materials for devices of the invention include those disclosed in U.S. Pat. Nos. 5,755,658; 5,667,778; 5,785,642; 6,098,629; 6,251,063; 6,251,064; 6,338,345; 6,358,197; and 6,401,718, the disclosures of which are incorporated in their entirety by reference hereto.

Hydrogels useful in the practice of the invention include lightly cross-linked biocompatible homopolymers and copolymers of hydrophilic monomers such as 2-hydroxylalkyl acrylates and methacrylates, e.g., 2-hydroxyethyl methacrylate (HEMA); N-vinyl monomers, for example, N-vinyl-2-pyyrolidone (N-VP); ethylenically unsaturated acids, for example, methacrylic acid (MA) and ethylenically unsaturated bases such as 2-(diethylamino)ethyl methacrylate (DE-AEMA). The copolymers may further include residues from non-hydrophilic monomers such as alkyl methacrylates, for example, methyl methacrylate (MMA), and the like. The cross-linked polymers are formed, by known methods, in the presence of cross-linking agents, such as ethyleneglycol dimethacrylate and methylenebis (acrylamide), and initiators such as 2,2-azobis(isobutyronit-rile), benzoyl peroxide, and the like, and radiation such as UV and gamma-ray.

Methods for the preparation of these polymers and copolymers are well known in the art. The Equilibrium Water Content (EWC) of these hydrogels can vary, e.g., from about 38% for Polymacon™ (poly HEMA) to about 79% for Lidofilcon™ B (a copolymer of N-VP and MMA) under ambient conditions.

Another type of hydrogel, useful in the practice of the invention, is illustrated by HYPAN™ hydrogel and poly(vinyl alcohol) (PVA) hydrogel. These hydrogels, unlike the aforementioned hydrogels, are not cross-linked. Their insolubility in aqueous media is due to their partially crystalline structures.

HYPAN™ hydrogel is a partially hydrolyzed polyacrylonitrile. It has a multiblock copolymer (MBC) structure comprising hard crystalline acrylonitrile blocks or hydrophilic blocks of acrylamide, which provide the hydrogel with good mechanical properties, and soft amorphous hydrophilic blocks to provide the hydrogel with good water binding capability.

HYPAN™ polymers are made from polyacrylonitrile polymer through acid catalyzed hydrolysis, which converts side nitrile groups into amide groups. The longer the reaction time, the higher the conversion rate. The higher the conversion rate of blocks of acrylonitrile units, the higher the hydrophilicity of the final block copolymer and the higher the water absorption properties of the system. In addition, based on the ability to dissolve in dimethylsulfoxide (DMSO) solvent, it is possible to fabricate various shapes and sizes of the systems based on HYPAN™ polymers. Possible shapes that can be fabricated out of HYPAN™ polymers include, but are not limited to blocks, sheets, films, spheres, beads, and strings.

Specific methods of preparing HYPAN™ hydrogels of different water contents and mechanical properties can be found in U.S. Pat. Nos. 4,337,327, 4,370,451, 4,331,783, 4,369,294, 4,420,589, 4,379,874 and 4,631,188 for example, the disclosures of which are incorporated herein by reference. The pre-nuclear forms of this material, for use in this invention, can be prepared by melt processing using solvents such as dimethyl formamide (DMF) and DMSO, as melting aids or by solution processing.

In one embodiment, bulking materials include inert, non-resorbable, biocompatible fluid solutions that when introduced into the body form a non-biodegradable solid mass that does not flow perceptibly under moderate stress, resists compression, tension and strain forces that tend to deform it, and retains a definite size and shape under ordinary conditions but that can be compressed. The liquid solution can include at least first and second fluid compounds that are separately injected and form a non-biodegradable solid mass at the site, e.g., by precipitation. Such a nonaqueous solution is a solution of a biocompatible polymer or prepolymer and a biocompatible solvent that can optionally include a contrast agent for facilitating visualization of the solution in the body. In one embodiment, a contrast agent is incorporated into the solution that precipitates into the solid mass or otherwise solidifies at the site of delivery. Such contrast agents can include biocompatible radiopaque materials that are either water-soluble or water insoluble.

Other biocompatible polymers that may be used in devices of the invention include those specifically set forth in the above-referenced U.S. Pat. No. 5,755,658 including cellulose acetates, ethylene vinyl alcohol copolymers, polyalkyl($C_1$-$C_6$) acrylates, acrylate copolymers, olyacrylonitrile, polyvinylacetate, cellulose diacetate, cellulose acetate butyrate, nitrocellulose, copolymers of urethane/carbonate, copolymers of styrene/maleic acid, and mixtures thereof.

The molecular weights of such polymers can be selected from the literature and are commercially available or can be prepared by art recognized, non-proprietary procedures. Polymers having a lower molecular weight will impart a lower viscosity to the composition as compared to higher molecular weight polymers. Accordingly, adjustment of the viscosity of the composition can be readily achieved by adjustment of the molecular weight of the polymer composition or polymer concentration in solution.

In one example, the weight average molecular weight, as determined by gel permeation chromatography, of suitable commercially available cellulose diacetate polymers having an acetyl content of from about 31 to about 40 weight percent can range between about 25,000 and about 200,000.

In another example, the weight average molecular weights of suitable polyacrylonitrile, polyvinylacetate, polyalkyl($C_1$-$C_6$) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically are at least about 50,000 and more preferably can range between about 75,000 and about 300,000.

Ethylene vinyl alcohol copolymers are either commercially available or can be prepared by art recognized procedures. Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

The overall hydrophobicity/hydrophilicity of a vinyl alcohol copolymer that, in turn, affects the relative water solubility/insolubility of the copolymer and the rate of precipitation of the copolymer in an aqueous solution is affected by the ratio of ethylene to vinyl alcohol in the copolymer. An exemplary vinyl alcohol copolymer comprises a mole percent of ethylene of from about 25 to about 60 and a mole percent of vinyl alcohol of from about 40 to about 75, more preferably a mole percent of ethylene of from about 40 to about 60, and a mole percent of vinyl alcohol of from about 40 to about 60. The ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C.

Other suitable materials can also be utilized as bulking materials in devices and methods of the invention. Such materials include suitable suspensions such as injectable bioglass of the type described in Walker et al., "Injectable Bioglass as a Potential Substitute for Injectable Polytetrafluorethylene Particles", J. Urol., 148:645-7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 and biocompatible compositions comprising carbon coated beads such as disclosed in U.S. Pat. No. 5,451,406 the disclosures of which are incorporated herein by reference. Such suitable materials for forming implants further include collagen and other biodegradable material of the type disclosed in U.S. Pat. No. 4,803,075 the disclosure of which is incorporated herein by reference, and other known injectable materials.

Still further materials that can be utilized as bulking materials in devices and methods of the invention include a suspension of smooth muscle cells in a biodegradable non-proteinaceous polymer solution that forms an ionically cross linked hydrogel having the cells dispersed therein when injected in vivo, which becomes a non-migratory, volume stable tissue mass as described in the above-referenced U.S. Pat. No. 5,667,778. In one embodiment, the smooth muscle cells are harvested from the patient.

Bulking devices of the invention can also have surface textures, coatings or structures to resist migration within the lumen wall. In general, the entire outer surface of the outer layer or filler can be coated or textured to facilitate tissue attachment such as by cellular ingrowth. The resulting attachment surface can be integral with the bulking device or can be directly or indirectly connected to the bulking device so that the bulking device can be positioned and retained in the desired position within the esophageal wall. The outer surface may additionally, or alternatively, be provided with any of a variety of tissue retention structures such as hooks, barbs, tacks, clips, sutures, staples, tissue adhesives, attachment strips, attachment spots, attachment connectors, or other attachment means which will be understood by those of skill in the art in view of the disclosure herein. The porosity of the cellular ingrowth surface may range from about 20 μm to about 100.0 μm or greater. In one embodiment, the porosity of the cellular ingrowth surface ranges from 20 μm to 50 μm and, in many embodiments, the porosity of the cellular ingrowth surface ranges from 20 μm to 30 μm.

In another embodiment, the bulking device can be contained in an outer coating that has at least one therapeutic substance dispersed therein. Examples of such materials can be found in U.S. Pat. Nos. 4,059,684; 5,879,697; 6,042,875; and 6,316,018 the disclosures of which are incorporated herein by reference.

Bulking devices of the invention also include at least one therapeutic substance. In one embodiment, the therapeutic substance is dispersed throughout substantially the entirety of the bulking material. An example of such a bulking device would be one made of a polymeric material, in which at least one therapeutic substance was dispersed within the precursor (s) to the bulking material. In other embodiments, the therapeutic substance(s) can be dispersed in a coating on the bulking material or in the outer vicinity of the bulking material.

Therapeutic substance, as used herein, can include any compound or biological material, which, in vivo is capable of producing an effect detectable by any chemical, physical or biological examination. A therapeutic agent will in general be any substance, which may be administered to a human or non-human animal body to produce a desired, usually beneficial, effect, and may be an agent having either a therapeutic or a prophylactic effect. In one embodiment, a therapeutic substance is one that will reduce or prevent an adverse physiological reaction from the tissue exposed to the bulking device of the invention. In another embodiment, a therapeutic substance is one that has a therapeutic or prophylactic effect related to the disease or condition for which the bulking device is being implanted.

Examples of therapeutic substances that can be incorporated into a bulking device of the invention include, but are not limited to antiplatelet agents, anti-coagulant agents, antimitotic agents, antioxidants, antimetabolite agents, anti-inflammatory agents, anti-infective agents, anti-cancer agents, antiproliferative, anti-angiogenesis, anti-thrombogenic, growth factors, acid reduction agents, and stem cells.

Examples of anti-infective agents that can be used in the invention include, but are not limited to, oxidizers, antibiotics, dehydrators, and membrane disruptors. Exemplary antiobiotics include, but are not limited to amoxicillin, ampicillin, bacampicillin, carbenicillin indanyl, mezlocillin, piperacillin, ticarcillin, amoxicillin-clavulanic acid, ampicillin-sulbactam, benzylpenicillin, colxacillin, dicloxacillin, methicillin, oxacillin, penicillin G, penicillin V, piperacillin+tazobactam, ticarcillin+clavulanic acid, nafcillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, cefuroxime axetil, loracaref, cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithroymcin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilimicin, streptomycin, tobramycin, paromomycin, teicoplanin, vancomycin, demeclocycline, doxycycline, methacycline, minocycline, oxytetracycline, tetracycline, chlortetracycline, mafenide, silver sulfadizine, sulfacetamide, sulfadizine, sulfamethoxazole, sulfasalazine, sulfisoxazole, trimethoprim-sulfamethoxaole, sulfamethizole, rifabutin, rifampin, rifapentine, linezolid, quinopristin+dalfopristin, bacitracin, chloramphenicol, colistemetate, fosfomycin, isoniazid, methenamine, metronidazol, mupirocin, nitrofurantoin, nitrofurazone, novobiocin, polymyxin B, spectinomycin, trimethoprim, colistin, cycloserine, capreomycin, ethionamide, pyrazinamide, para-aminosalicyclic acid, and erythromycin ethylsuccinate+sulfisoxazole.

Examples of anti-inflammatory agents can include, but are not limited to aspirin, salsalate, choline magnesium trisalicylate, etodolac, and indomethacin. In one embodiment of the invention, antibiotic agents can include, but are not limited to, penicillin, cefoxitin, oxacillin, tobramycin, gentamicin, ciprofloxacin, minocycline, rifampin. Examples of antiplatelet agents can include, but are not limited to aspirin, dipyridamole, clopidogrel bisulfate, ticlopidine hydrochloride, abciximab, tirofiban hydrochloride, and cilostazol. Examples of anti-cancer agents include, but are not limited to darbepoetin, irinotecan, cyclophosphamide, oxaliplatin, gemcitabine, imatinib, trastuzumab, gefitinib, chlorambucil, dronabinol, gemtuzumab, pegfilgrastim, epoetin alfa, methotrexate, bortezomib, and leucovorin. Anticoagulant agents can include, but are not limited to, heparin, protamine, hirudin, warfarin, enoxparin, tick anticoagulant protein, and sodium citrate. Antimitotic agents and antimetabolite agents can include, but are not limited to, methotrexate, azathioprine, vincristine, vinblastine, 5-fluorouracil, adriamycin and mutamycin. Examples of anti-thrombogenic agents include, but are not limited to, taxol, and heparin. Acid reduction agents can include, but are not limited to, $H_2$ receptor antagonists, proton pump inhibitors, and motility enhancers. Examples of $H_2$ receptor antagonists include, but are not limited to cimetidine, famotidine, nizatidine, and ranitidine. Examples of proton pump inhibitors include, but are not limited to lansoprazole, omeprazole, esomeprazole, rabeprazole, and pantropazole. Examples of motility enhancers include, but are not limited to cholinergic receptor agonists, motilin receptor agonists, and dopamine receptor antagonists. Examples of cholinergic receptor agonists include, but are not limited to cisapride, bethanechol, and tegaserod. An example of a motilin receptor agonist includes, but are not limited to erythromycin. Examples of dopamine receptor antagonists include, but are not limited to metoclopramide, and domperidone. Embodiments of the invention can also include one or more agents to decrease the absorption of one or more specific nutrients. An example of an agent that decreases the absorption of one or more specific nutrients is orlistat. Orlistat is a lipase inhibitor, i.e. it inhibits the absorption of lipids (fats) into the stomach and small intestine.

Embodiments of the invention are implanted through the mucosa, into the submucosa of a lumen wall. Because mucosa, for example of the gastrointestinal or urinary tract, is generally non-sterile, there is always the potential for infection. Therefore, in one embodiment of the invention, a bulking device includes as a therapeutic substance, one more anti-infective agents. Examples of anti-infective agents that can be used in the invention include, but are not limited to, oxidizers, antibiotics, dehydrators, and membrane disruptors. In one embodiment, the antibiotics can include, but are not limited to, ciprofloxcin, minocycline, rifampin, penicillin, cefoxitin, oxacillin, tobramycin, gentamicin, and combinations thereof. In one embodiment, a combination of minocycline, and rifampin is used as a therapeutic substance in a bulking agent of the invention.

The therapeutic substance can be incorporated by dissolving or suspending them in the precursor of the bulking material. If the therapeutic substances are suspended in the solution, they can be dispersed as fine particles ranging from 1-100 microns in average particle size. Alternatively, if a polymer having a relatively low melting point is used, the polymer and therapeutic substance can be blended in the molten stage (such as by casting or coextrusion) if the therapeutic substance does not degrade at the molten temperature.

The concentration or loading of the therapeutic substance in the bulking material may be varied according to the therapeutic effects desired. Also, the loading, in terms of the ratio of therapeutic substance to the precursor of the bulking material, will depend upon the rate at which the bulking material is to release the therapeutic substance to the body tissue. Generally, the bulking material may contain 0.1-90% by weight or in another embodiment 10-45% by weight of the therapeutic substance. In yet another embodiment, 25-40% by weight of the therapeutic substance should be incorporated in the bulking material.

The invention also includes methods of altering at least a portion of a lumen wall that includes the steps of piercing the mucosa of the lumen wall to be augmented, introducing a bulking device within the submucosa, wherein the bulking device is configured to alter the portion of the lumen into which it is implanted, and closing the mucosal opening. In one embodiment, the bulking device can be implanted into the muscularis layer of the lumen wall.

In one embodiment, the bulking material with the therapeutic substance associated therewith can be injected directly into the submucosa to form the bulking device therein. Alternatively, a space can first be formed in the submucosa by injection of saline solution other aqueous or physiologic solution into the submucosa to form a blister. The blister of saline solution other aqueous or physiologic solution within the space disperses into the body after injection of and solidification of the implant forming solution into the mass of bulking agent. In one embodiment of the invention, the mucosa is pierced with either a needle, an electrocautery cutter, a dissection tool, or some combination thereof. In yet another embodiment, a pouch is created within the submucosa before the bulking device is introduced. The pouch can be created by injecting a volume of fluid through the pierced mucosa, utilizing a dissection tool to created a blunt dissection between two adjacent tissue planes, utilizing an inflation device, or a combination of any of these methods. In one embodiment where fluid is used to create a pouch, the fluid is saline. In another embodiment, the mucosal opening can be closed with a suture, ligating bands, staples, clips, surgical adhesive or some combination of those items.

In one embodiment of the invention, the bulking devices can be implanted with and/or the methods can be carried out with devices, as described in U.S. Pat. Nos. 6,098,629; 6,338, 345; and 6,401,718. Alternatively, other surgical tools and/or devices can be utilized to implant the bulking devices of the invention within lumen walls of a patient. In one embodiment, a grasper, a clamshell deployment device, a hollow catheter, an instrument lumen, or some combination of those tools are utilized.

Devices of the invention can be implanted into or around the vicinity of the LES for the treatment or management of gastroesophageal reflux disorder (GERD). In such an embodiment, the bulking material of the device is generally configured to enhance the functioning of the LES. The therapeutic substance or substances are generally chosen to minimize or reduce the possibility of infection, minimize or reduce possible adverse response of the tissue to the bulking device, treat one or more possible causes or side-effects of GERD (i.e. excess acid production), treat or prevent possible complications of GERD (Barret's esophagus or esophageal cancer), or some combination thereof.

Figure 3:
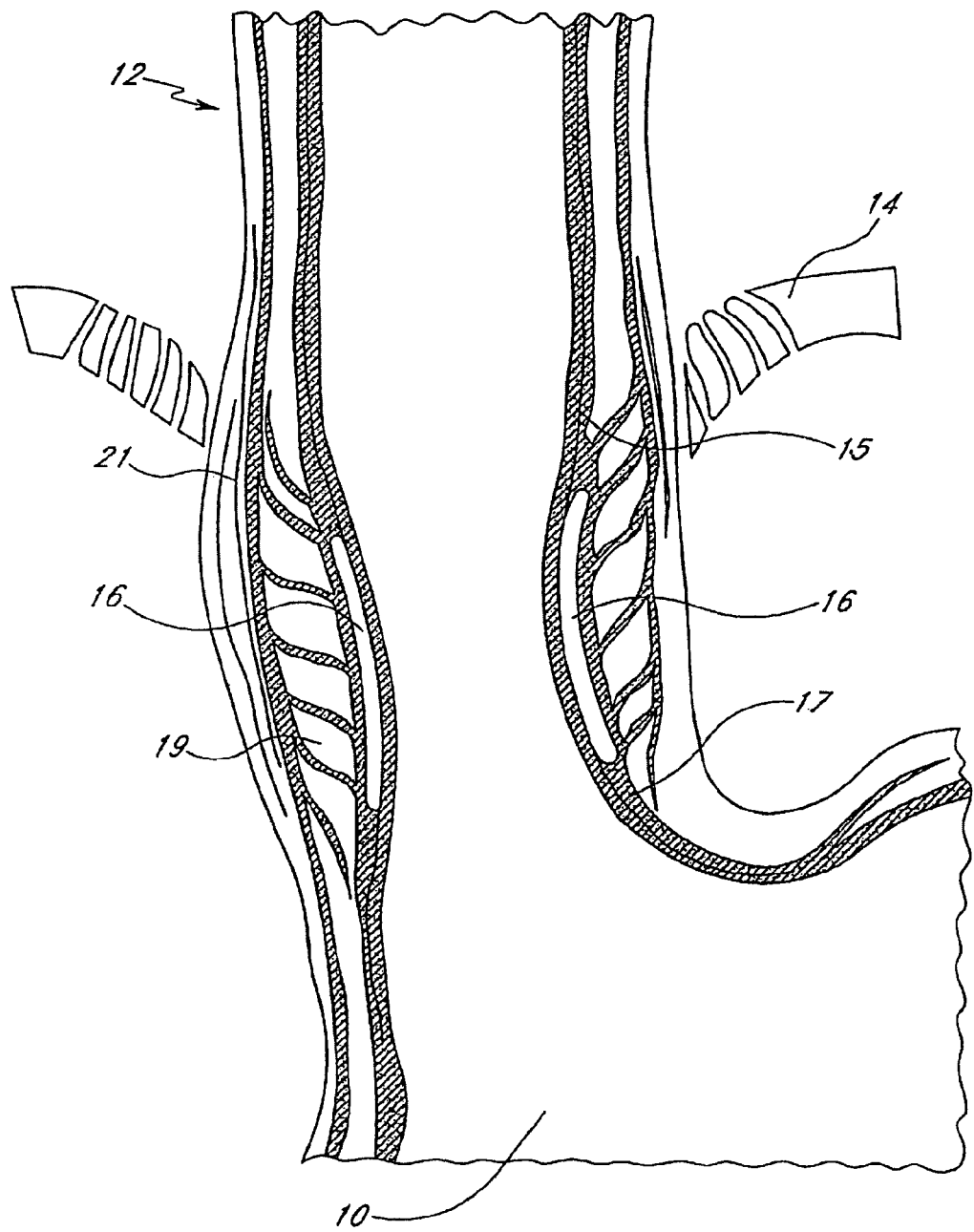
FIG. 3 depicts a bulking device of the invention implanted in the vicinity of the lower esophageal sphincter (LES).

Referring to FIG. 3 there is illustrated a schematic representation of the stomach 10 and a portion of the lower esophagus 12. The esophagus 12 extends through the diaphragm 14, below which the esophagus 12 communicates with the interior of the stomach 10. A pair of gastroesophageal prosthetic bulking devices 16, in accordance with the present invention, are illustrated at about the junction between the lower esophagus 12 and the stomach 10.

In the illustrated embodiment, the bulking device 16 is implanted in the submucosa 17. The submucosa 17 is a fibrous layer of tissue positioned between the mucosa 15 and a layer of circular muscle 19. The circular muscle 19 is surrounded by a layer of longitudinal muscle 21, as is well understood in the art. The bulking device 16 is preferably implanted beneath the mucosa 15 as is discussed elsewhere herein. The bulking device 16 may either be implanted within the submucosa 17 as illustrated, or at the interface of adjacent tissue planes, such as between the mucosa 15 and submucosa 17, or between the submucosa 17 and circular muscle 19. Preferably, the bulking device 16 is implanted radially inwardly from the circular muscle layer 19.

Although the anatomy illustrated in FIG. 3 is generally normal, except for the improperly functioning native lower esophageal sphincter, the present invention is also useful in patients having lower esophageal abnormalities, such as hiatal hernia. In this condition, a portion of the wall of the stomach 10 extends upwardly through the diaphragm 14 and herniates superiorly to the diaphragm 14. The existence of a hiatal hernia or another abnormality in the lower esophagus may affect the implanted location of the esophageal prosthetic bulking device 16, but may not disqualify a patient otherwise treatable with the prosthetic bulking device 16 of the present invention.

Ideally, the esophageal bulking device 16 is implanted in a position that extends across or is closely adjacent the sphincter so that residual sphincter activity is optimized and the mucosal regions of the esophagus are protected from acid reflux. The precise positioning of the implant 16 depends largely on the patient's anatomy and the severity of GERD, and will be a matter of clinical choice at the time of implantation. In patients with a hiatal hernia, for example, the esophageal bulking device 16 is implanted as close as possible to the sphincter but care must be taken to insure that the hernia will not perturb the operation of the bulking device.

In an embodiment where a bulking device is configured to treat GERD, the objective of the present invention is to increase the closing pressure of the LES. It is believed that a closing pressure of at least a certain minimum closing threshold value, maintained along a minimum axial effective LES length will satisfactorily reduce esophageal reflux. In the intra-abdominal (i.e., inferior to the diaphragm) esophagus, about 2 cm of effective LES length appears desirable. An average pressure along that length is generally in excess of about 10 mm Hg, in another embodiment at least about 15 mm Hg, and in yet another embodiment in the range of from about 15 mm to about 30 mm Hg.

Within certain outer limits, any increase in the closing pressure in the LES may improve symptoms. For example, some patients have an LES closing pressure on the order of about 5 mm Hg, which is accompanied by severe GERD symptoms. At the high end, a closing pressure in excess of about the minimum diastolic pressure inhibits blood flow, thereby increasing the risk of localized pressure necrosis. Pressure slightly below the minimal diastolic pressure may still interfere with swallowing function. The present invention can therefore enable an increase in the closure pressure from a pretreatment value below about 10 to 15 mm Hg to a post treatment value of on the order of from about 18 or 20 to about 25 or 30, along a length of at least about 1.0 cm and in another embodiment at least about 2 cm or 2.5 cm or more.

Suitable bulking devices for implantation into the esophagus include a soft, flexible body that may have an expanded axial length from 0.5 cm to 5.0 cm, a width (circumferential direction) of 0.2 cm to 2.0 cm, and a thickness (radial direction) of 0.2 cm to 2.0 cm. Many esophageal bulking devices of the present invention have a length within the range of 1.0 cm to 4.0 cm, a width within the range of 0.2 cm to 1.5 cm, and a thickness within the range of 0.2 cm to 1.5 cm. In one embodiment, the esophageal bulking device has a length of 2.0 cm to 3.0 cm, a width of 0.8 cm to 1.0 cm, and a thickness of 0.4 cm to 0.6 cm. The cross-sectional configuration may be circular, oval or other configuration, as desired.

Length to thickness ratios are generally no more than about 15:1 and are often no more than about 6:1 or 4:1. Length to thickness ratios on the order of less than 3:1 may also be desirable depending upon the severity of the condition. The cross-sectional area of the bulking device may also vary at different points along the length of the same device. As mentioned above, optimal dimensions may be patient specific and can be determined through routine experimentation of one of skill in the art in view of the disclosure herein.

An LES having a relaxed open diameter of 2.0 cm, for example, has a cross-sectional lumen area of $3.14\ cm^2$. A 25% bulking function could be accomplished by providing a bulking device having a total cross-sectional area in the bulking zone of about $0.785\ cm^2$. The bulking area may represent the area of an esophageal bulking device having a generally oval or rectangular cross-section (e.g., 0.443 cm.times.1.772 cm), which is adapted to extend axially for a length of 1 to 3 cm beneath the mucosa.

In one embodiment where the bulking device is to be implanted into or around the vicinity of the lower esophageal sphincter (LES), the therapeutic substance can include an acid reduction agent, an anti-cancer agent, an anti-infective agent, an anti-inflammatory agent, or some combination thereof. In one embodiment, a device of the invention for implantation into or around the LES includes at least one of an acid reduction agent, an anti-cancer agent, an anti-infective agent, and an anti-inflammatory agent. Acid reduction agents can include, but are not limited to, $H_2$ receptor antagonists, proton pump inhibitors, and motility enhancers. Examples of $H_2$ receptor antagonists include, but are not limited to cimetidine, famotidine, nizatidine, and ranitidine. Examples of proton pump inhibitors include, but are not limited to lansoprazole, omeprazole, esomeprazole, rabeprazole, and pantropazole. Examples of motility enhancers include, but are not limited to cholinergic receptor agonists, motilin receptor agonists, and dopamine receptor antagonists. Examples of cholinergic receptor agonists include, but are not limited to cisapride, bethanechol, and tegaserod. An example of a motilin receptor agonist includes, but are not limited to erythromycin. Examples of dopamine receptor antagonists include, but are not limited to metoclopramide, and domperidone. Embodiments of the invention for the treatment of GERD can also include, as the therapeutic substance, sucralfate, misoprostol, and other similar substances. Embodiments to treat GERD can also include one or more anti-infective agents. Examples of anti-infective agents that can be used in the invention include, but are not limited to, oxidizers, antibiotics, dehydrators, and membrane disruptors. In one embodiment, the antibiotics can include, but are not limited to, ciprofloxcin, minocycline, rifampin, penicillin, cefoxitin, oxacillin, tobramycin, gentamicin, and combinations thereof. In one embodiment, a combination of minocycline, and rifampin is used as a therapeutic substance in a bulking agent of the invention.

Figure 4:
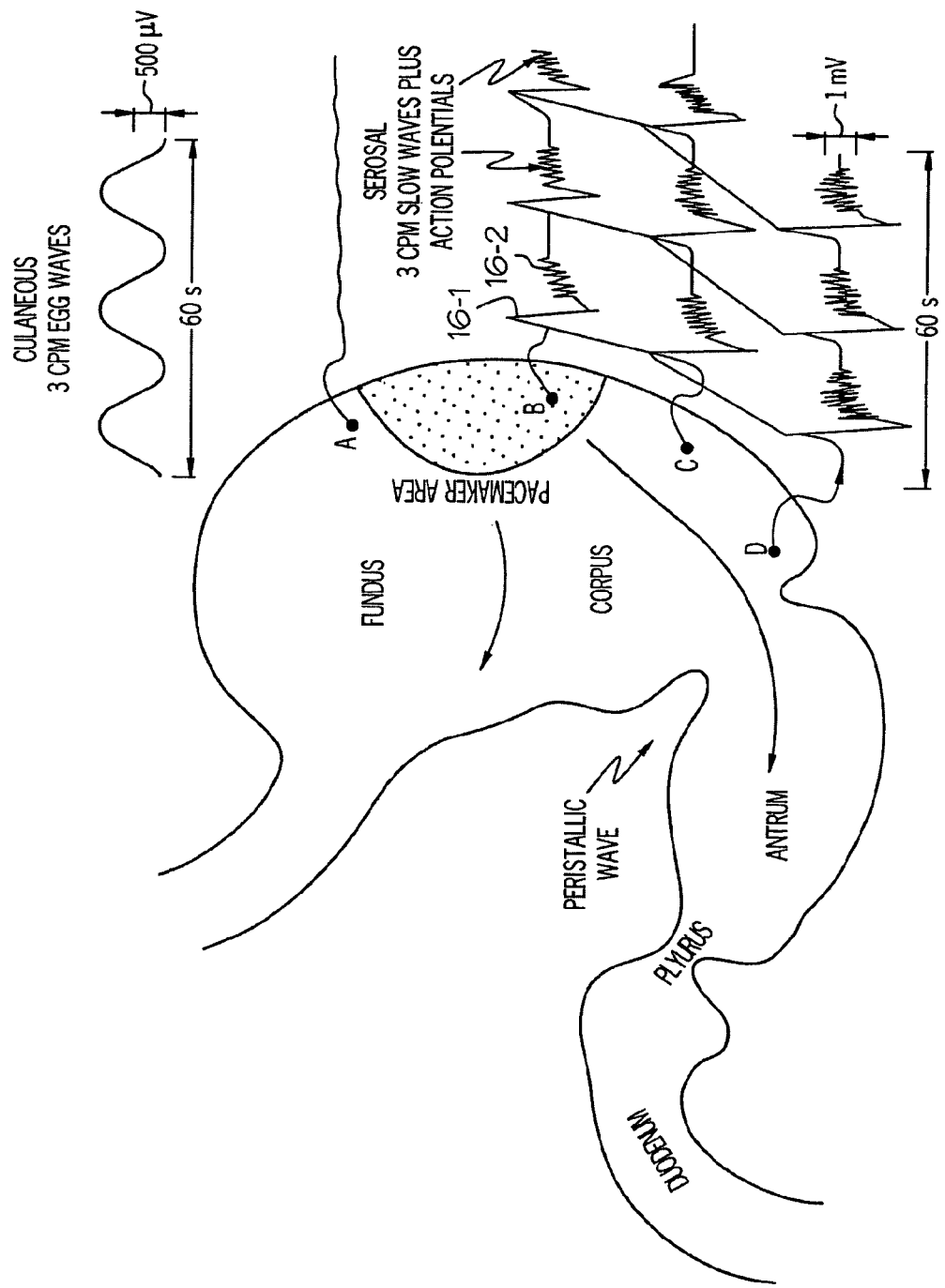
FIG. 4 depicts various portions of a stomach and information regarding electrical activity thereof.

Another embodiment of the invention can be configured to be implanted in the vicinity of or around the vicinity of the pyloric sphincter to treat obesity. Food is ingested until a feeling of satiety is induced and/or the stomach is distended. During ingestion and for a time thereafter, the smooth muscle layers of the pyloric sphincter are contracted to restrict the pylorus lumen and keep food in the stomach until it is liquefied. The ingested food bolus is propelled aborally mixed and ground in the antrum against the closed pylorus, and then retro-propelled orally into the more proximal corpus. The muscles of the stomach rhythmically churn ingested food and digestive juices into a semi-liquid mass called chyme. The stomach muscles contract peristaltic waves triggered by a gastric pacemaker region shown in FIG. 4 and move downward or retrograde toward the pylorus and mix and shear the food into chyme while the pylorus lumen is closed. After the ingested food is ground into chyme, the pyloric sphincter relaxes in concert with antral motor activity of each peristaltic wave and lets some chyme pass into the duodenum. The pylorus lumen is small enough to function as a sieve to only let minute food particles enter the duodenum in the absence of active contraction of the pyloric sphincter.

Retaining food in the stomach for a prolonged time promotes a prolonged "full" feeling and discourage further food intake. Implantation of a bulking device in the vicinity of the pyloric sphincter can treat obesity by inducing a partial pyloric obstruction or small intestine obstruction to prolong emptying of the stomach or small intestine to induce the patient to refrain from eating frequently or eating too much.

Figure 5:
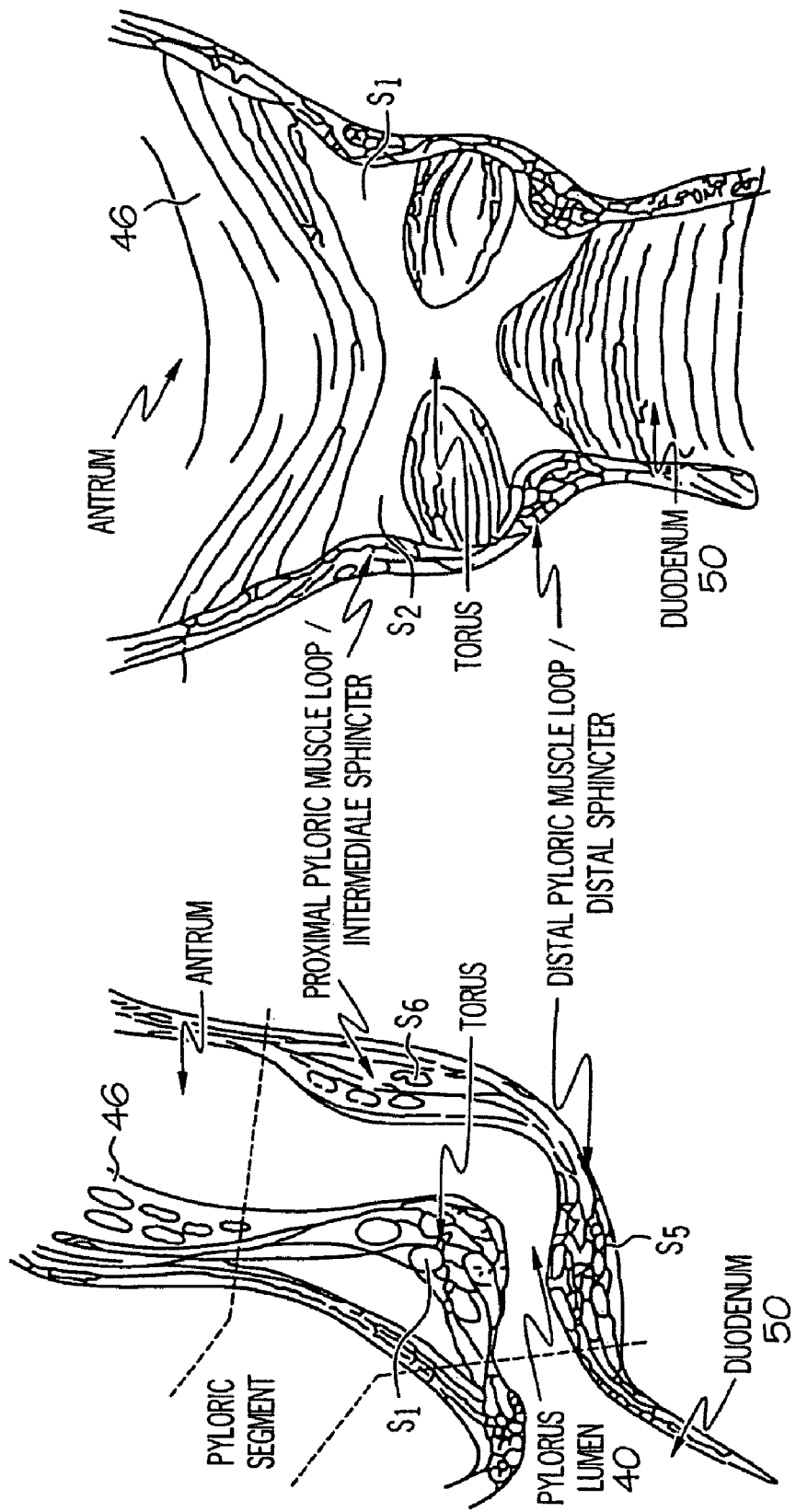
FIG. 5 depicts the pylorus between the stomach and the duodenum.

FIG. 5 depicts the pylorus 34 between the stomach 14 and the duodenum 50 in greater detail. In the illustrated embodiments, the bulking device(s) can be implanted within the submucosa 44 between the mucosal surface or mucosa 46 and the pyloric sphincter 48.

A pylorus lumen having a relaxed open diameter of 2.0 cm, for example, has a cross-sectional lumen area of $3.14\ cm^2$. A 25% bulking function could be accomplished by providing a bulking device 16 having a total cross-sectional area in the bulking zone of about $0.785\ cm^2$. The bulking area may represent the area of a bulking device having a generally oval or rectangular cross-section (e.g., 0.443 cm×1.772 cm) that is adapted to extend axially for a length of 1 to 3 cm beneath the mucosa.

In one embodiment where the bulking device is to be implanted into or around the vicinity of the pyloric sphincter to treat obesity, the therapeutic substance can include an anti-infective agent, an anti-inflammatory agent, an agent to decrease the absorption of specific nutrients, or some combination thereof. In one embodiment, a device of the invention for implantation into or around the pyloric sphincter includes at least one of each of an anti-infective agent, an anti-inflammatory agent, and an agent to decrease the absorption of one or more specific nutrients. An example of an agent that decreases the absorption of one or more specific nutrients is orlistat. Orlistat is a lipase inhibitor, i.e. it inhibits the absorption of lipids (fats) into the stomach and small intestine. Embodiments to treat obesity can also include, as a therapeutic substance, one or more motility enhancers. Examples of motility enhancers include, but are not limited to cholinergic receptor agonists, motilin receptor agonists, and dopamine receptor antagonists. Examples of cholinergic receptor agonists include, but are not limited to cisapride, bethanechol, and tegaserod. An example of a motilin receptor agonist includes, but are not limited to erythromycin. Examples of dopamine receptor antagonists include, but are not limited to metoclopramide, and domperidone. Embodiments of the invention for the treatment of obesity can also include, as the therapeutic substance, sucralfate, misoprostol, and other similar substances. Embodiments to treat obesity can also include one or more anti-infective agents. Examples of anti-infective agents that can be used in the invention include, but are not limited to, oxidizers, antibiotics, dehydrators, and membrane disruptors. In one embodiment, the antibiotics can include, but are not limited to, ciprofloxcin, minocycline, rifampin, penicillin, cefoxitin, oxacillin, tobramycin, gentamicin, and combinations thereof. In one embodiment, a combination of minocycline, and rifampin is used as a therapeutic substance in a bulking agent of the invention. Embodiments for the treatment of obesity can also include, as a therapeutic substance, a substance that decreases gastrointestinal motility. Examples of substances that decrease gastrointestinal motility include, but are not limited to opioids, and 5-$HT_3$ receptor antagonists. A specific example of a 5-$HT_3$ receptor antagonist is alosetron.

Figure 6:
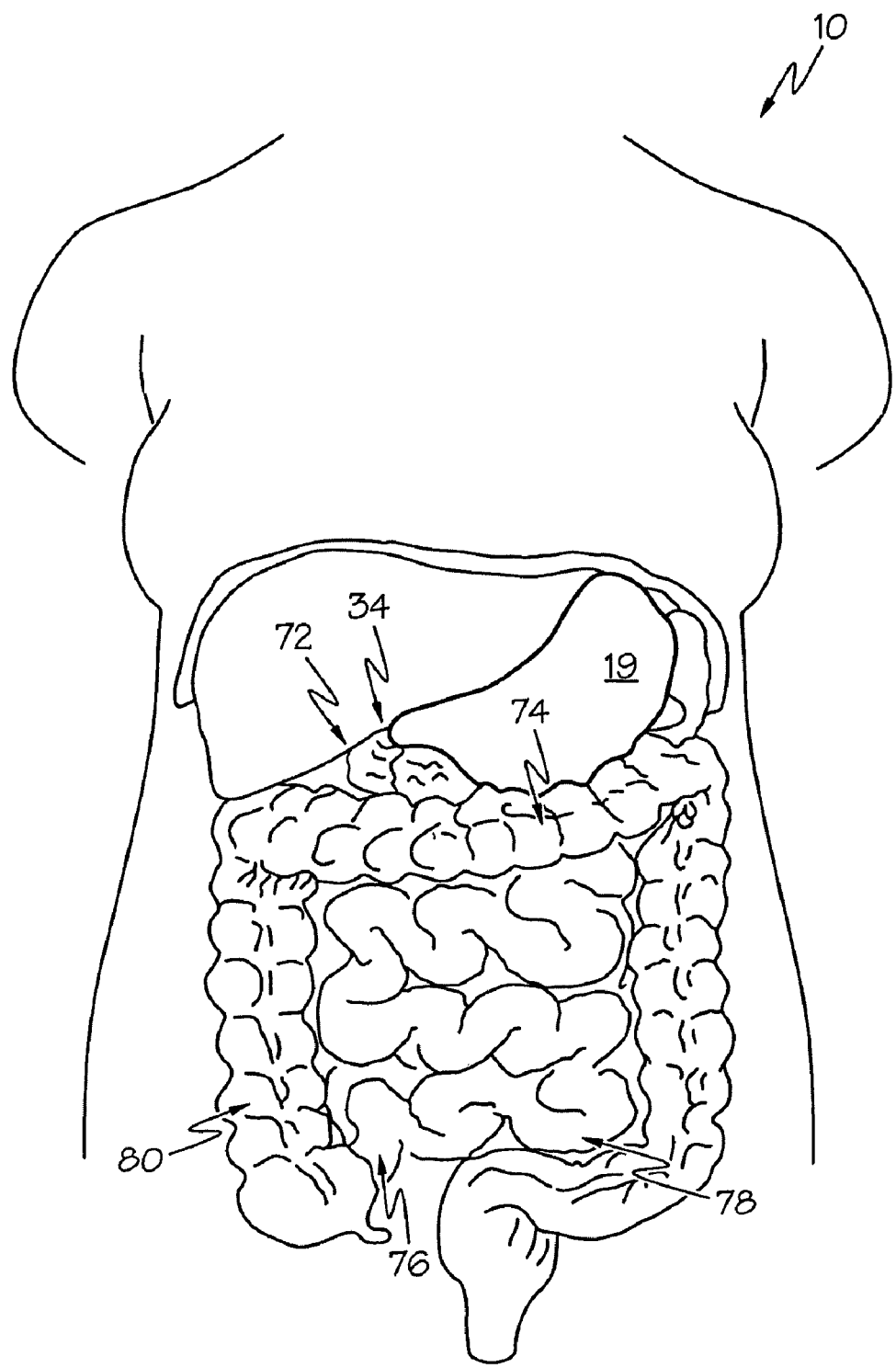
FIG. 6 depicts alternative positions within the gastrointestinal tract where bulking devices of the invention can be implanted.

FIG. 6 is a schematic illustration of the GI tract identifying other potential implantation sites of one or more bulking devices to restrict a lumen and slow emptying of the contents of the stomach 14, duodenum 50 or small intestines 78. The particular sizes, configurations, and therapeutic substances of the bulking devices can be selected by the surgeon to meet the needs of the particular patient and the implantation location.

Implantation within the duodenum 50 can be adjacent the first flexure (flexura duodenisuperior) 72 or adjacent the duodenojunal flexure 74. One or more bulking devices can be implanted endoscopically within the wall of the duodenum in a manner similar to the above-described procedure for insertion of the same in relation to the pylorus 34.

One or more bulking devices can be implanted within the wall of the ileocecal sphincter 76 at the junction of base of the ascending colon 80 and the small intestine 78. The ileocecal sphincter 76 opens to allow partially digested chyme to move from the small intestine 78 to the colon 80. Partially constricting the ileocecal sphincter 76 when it is normally relaxed would limit the movement of partially digested food from the small to large intestine, creating a condition similar to pseudo-obstruction (with attendant symptoms of nausea, vomiting, abdominal pain in association with eating). One or more bulking devices can be implanted with the aid of a sigmoidscope or a laparascope within the wall of the ileocecal sphincter 76 in a manner similar to the above-described procedure for insertion of the same in relation to the pylorus 34.

Figure 7:
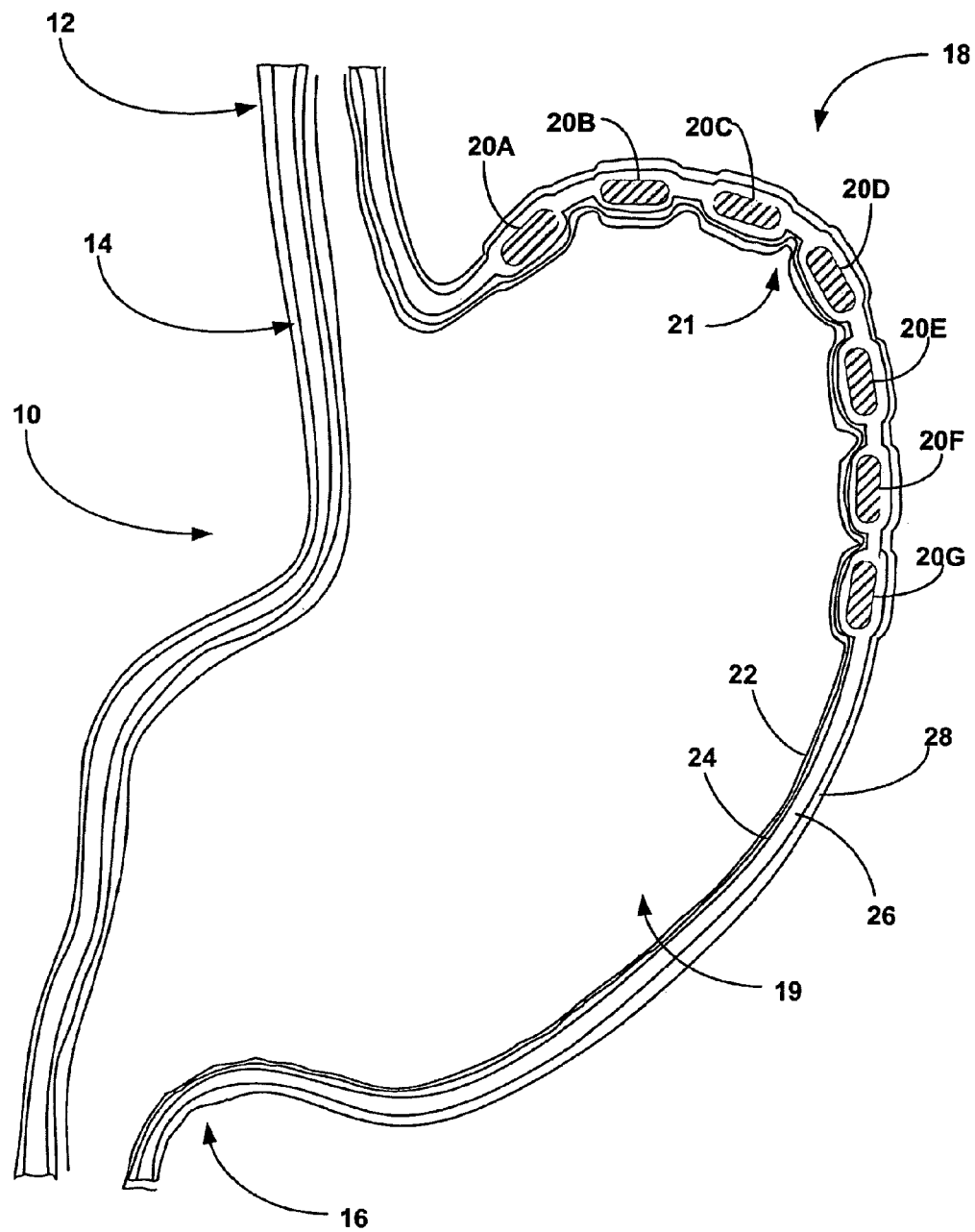
FIG. 7 depicts a stomach with a number of bulking devices implanted in the fundus.

Bulking devices of the invention can also be implanted within the stomach wall to treat obesity. FIG. 7 is a cross-sectional diagram of the interior of a stomach 10, including esophagus 12, lower esophageal sphincter 14, pyloric sphincter 16, fundus 18, and corpus 19, with bulking devices 20A-20G (hereinafter bulking devices 20) implanted in stomach wall 21. For example, bulking devices 20A-20G can be implanted in the muscle layer of the stomach. Alternatively, bulking devices 20A-20G can be implanted in the mucosa or submucosa of stomach 10.

In FIG. 7, bulking devices 20 are depicted in an enlarged state with a size sufficient to bias stretch receptors within stomach wall 21. Each of bulking devices 20 exerts a localized stretching force on stretch receptors in stomach 10. The stretch receptors are coupled to the enteric nervous system of a patient. When triggered by the stretching force, the stretch receptors induce a sensation of satiety in the patient, and discourage the patient from consuming an excessively large meal.

Bulking devices 20 bias stomach wall 21 into a pre-stretched condition that either triggers the stretch receptors or causes earlier triggering of the stretch receptors during the consumption of a meal. Hence, even though the stomach may not contain a substantial portion of food at the outset of a meal, implanted bulking devices 20 have already biased the stretch receptors into a condition that simulates the presence of a substantial portion of food. Consequently, during the course of a meal, stomach 10 requires a smaller amount of food to produce a sensation of satiety, which causes the patient to stop eating.

In this manner, bulking devices 20 do not significantly change the size or contents of stomach 10, but provide a physiological modification of stomach wall 21. This modification affects the response of the patient's enteric nervous system and the amount of food consumed by the patient, thereby preventing increased obesity and possibly causing or assisting in weight loss. In some cases, bulking devices 20 may be explanted after a desired course of obesity treatment has been achieved.

Bulking devices 20 may be endoscopically implanted, avoiding the need for surgery. As further shown in FIG. 7, bulking devices 20 may be implanted within stomach wall 21 throughout fundus 18 at spaced apart positions to provide localized stretching at several different points. Bulking devices 20 may be implanted in other regions of stomach 10, other than fundus 18, such as corpus 19. However, stretch receptors tend to be concentrated within fundus 18. Accordingly, in some embodiments, bulking devices 20 may be primarily or solely provided within fundus 18, where they are expected to be most effective in biasing stretch receptors. In other words, according to some embodiments, bulking devices 20 may be generally located only within fundus 18 and nowhere else. In other embodiments, bulking devices 20 may be implanted within fundus 18 and corpus 19, or solely within corpus 19.

Bulking devices 20 are implanted within stomach wall 21. Stomach wall 21 of a human stomach 10 generally includes four layers. With reference to FIG. 7, the innermost layer, mucosa 22, generates digestive juices. Submucosa 24 contains blood vessels that provide blood and oxygen to mucosa 22. Muscularis 26, a smooth muscle layer embedded with nervous plexus, contracts to mix food with digestive juices generated by mucosa 22. Serosa 28, the fourth and outermost layer, protects the other layers and confines digestive juices to stomach 10.

As one example, bulking devices 20 may be implanted within muscularis 26, which contains the stretch receptors. The stretch receptors are coupled to the nervous system via the vagus nerves, and signal the patient when stomach 10 reaches a stretch point indicating a large quantity of food. With bulking devices 20, the patient perceives that the stomach has reached a stretch point indicating fullness much earlier during the course of the meal and at a point at which the stomach is not actually full. In other embodiments, bulking devices 20 may be implanted within mucosa 22 or submucosa 24.

Figure 8:
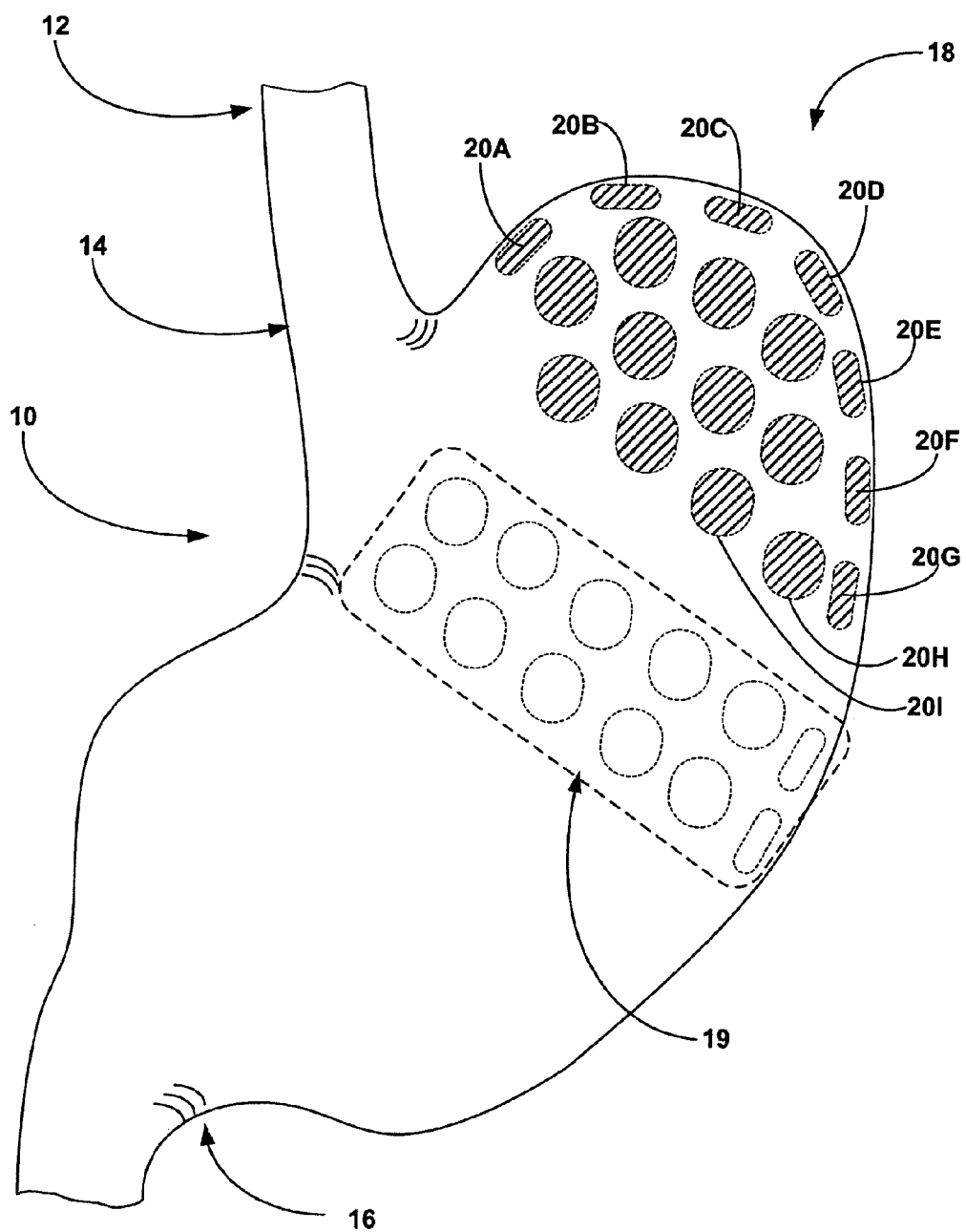
FIG. 8 depicts a stomach with a number of bulking devices implanted in the fundus and in shadow, in the corpus.

FIG. 8 is a diagram of the exterior of stomach 10 with implanted bulking devices 20. As shown in FIG. 8, bulking devices 20 may be implanted at spaced apart positions within fundus 18 of stomach 10. FIG. 8 includes additional reference numerals 20H, 20I to identify some of the additional bulking devices 20 in the wall 21 of stomach 10. Bulking devices 20 may be implanted on an anterior, posterior and lateral wall of fundus 18 so as to extend generally about the entire fundus region. Also, in some embodiments, bulking devices 20 may be implanted in the corpus, as indicated by the bulking devices associated with reference numeral 19 in FIG. 8.

FIG. 8 depicts only an anterior side of fundus 18 for ease of illustration. It should be understood, however, that an array of bulking devices 20 as depicted on the anterior side may likewise be implanted on a posterior side of fundus 18, or corpus 19. In other embodiments, bulking devices 20 may be implanted on a single side or two sides, i.e., posterior, anterior, and/or lateral. In each case, bulking devices 20 are implanted as relatively small solid objects that then expand when they rehydrate following implantation, and thereby bias the stretch receptors in fundus 18 of stomach 10.

In the example of FIG. 8, bulking devices 20 have a substantially disc-like shape. In other embodiments, bulking devices 20 may have a variety of shapes, e.g., substantially spherically shaped, rod- or cylinder-shaped, or irregularly shaped, as will be described. In an at least partially dehydrated state for implantation, the disc-like shape of bulking devices 20 in FIG. 8 may have a thickness of approximately 1 mm to 2 mm, and a diameter of approximately 10 mm to 15 mm. Following implantation in stomach wall 21 and subsequent rehydration, the disc-like shape may expand to have a thickness of approximately 4 mm to 6 mm, and a diameter of approximately 8 mm to 10 mm. Hence, in some embodiments, the disc-like shape of bulking device 20 may exhibit expansion in thickness, but contraction in diameter, following implantation.

In an at least partially dehydrated state for implantation, disk-like bulking devices 20 may have a volume in a range of approximately 75 mm$^3$ to 350 mm$^3$. Upon expansion following implantation, bulking devices 20 may have a volume in a range of approximately 200 mm$^3$ to 470 mm$^3$. Hence, each bulking device 20 may have a volumetric expansion ratio, from an at least partially dehydrated state (pre-implantation) to a hydrated, expanded state (post-implantation), of at least approximately 4.5:1, and more particularly approximately 27:1.

As a further illustration, if constructed as an elongated rod- or cylinder-like member, the hydrogel material may exhibit pre-implantation dimensions of less than or equal to approximately 2 mm in diameter by approximately 20 mm in length, and post-implantation dimensions of greater than or equal to approximately 6 mm in diameter by approximately 15 mm. This corresponds to an exemplary pre-implantation volume of less than approximately 65 mm$^3$, and a post-implantation volume of greater than or equal to approximately 400 mm$^3$.

Hence, in general, the pre-implantation volume of a bulking device 20 is less than or equal to 100 mm$^3$ and the post-implantation volume of a bulking device is greater than 200 mm$^3$. In some embodiments, the pre-implantation volume of bulking device 20 is less than or equal to approximately 75 mm$^3$, and the post-implantation volume of the bulking device is greater than or equal to approximately 300 mm$^3$.

Spacing between adjacent bulking devices 20 may be controlled by taking into account the expanded size of the bulking devices. The outer perimeters of adjacent, expanded bulking devices 20 may be separated by a distance in range of approximately 3 mm to 10 mm, and more particularly approximately 3 mm to 5 mm. Adjacent bulking devices 20 are separated by a section of intact muscularis, mucosa or submucosa, and provide a localized stretching effect. By leaving a substantial portion of the muscularis, mucosa, or submucosa intact, bulking devices 20 can bias the stretch receptors without compromising the contractile function of the stomach wall 21 in support of the digestion process.

In other embodiments, however, an array of bulking devices 20 may be placed so that, upon expansion, the outer perimeters of the bulking devices actually come into contact with one another. In this manner, bulking devices 20 may cooperate to provide an overall stretching effect to a larger region of fundus 18. Bulking devices 20 may be placed in a plurality of regions, while leaving other areas of the muscularis between regions intact.

Whether bulking devices are spaced apart or implanted to contact one another upon expansion, the bulking devices do not expand wall 21 of stomach 10 like consumption of a meal would, in which case the entire stomach wall would tend to stretch outward as a unitary body. Instead, bulking devices 20 provide localized or regional stretching of selected portions of fundus 18 to trigger the stretch receptors, and cause a false sensation of fullness that induces early satiety.

Bulking devices of the invention can also be used to partially obstruct the esophagus to treat obesity. Partial obstruction in the esophagus serves to limit food intake by a patient, and thereby treat obesity. In particular, a partial obstruction is sized to permit passage of food, but at a reduced intake rate relative to an unobstructed esophagus. An inner lumen of a typical human esophagus has a diameter of approximately 2.5 to 3.5 cm. A partial obstruction may be sized to reduce the effective diameter of inner lumen to approximately 1.0 to 2.0 cm at the obstruction point. With a partial obstruction, the patient is incapable of consuming food at an excessive rate, and experiences discomfort during excessive food consumption. The partial obstruction physically limits excessive food consumption through the inner lumen. At the same time, the discomfort may provide a form of biofeedback that discourages the patient from excessive eating. The result is prevention of increased obesity and weight loss.

Figure 9:
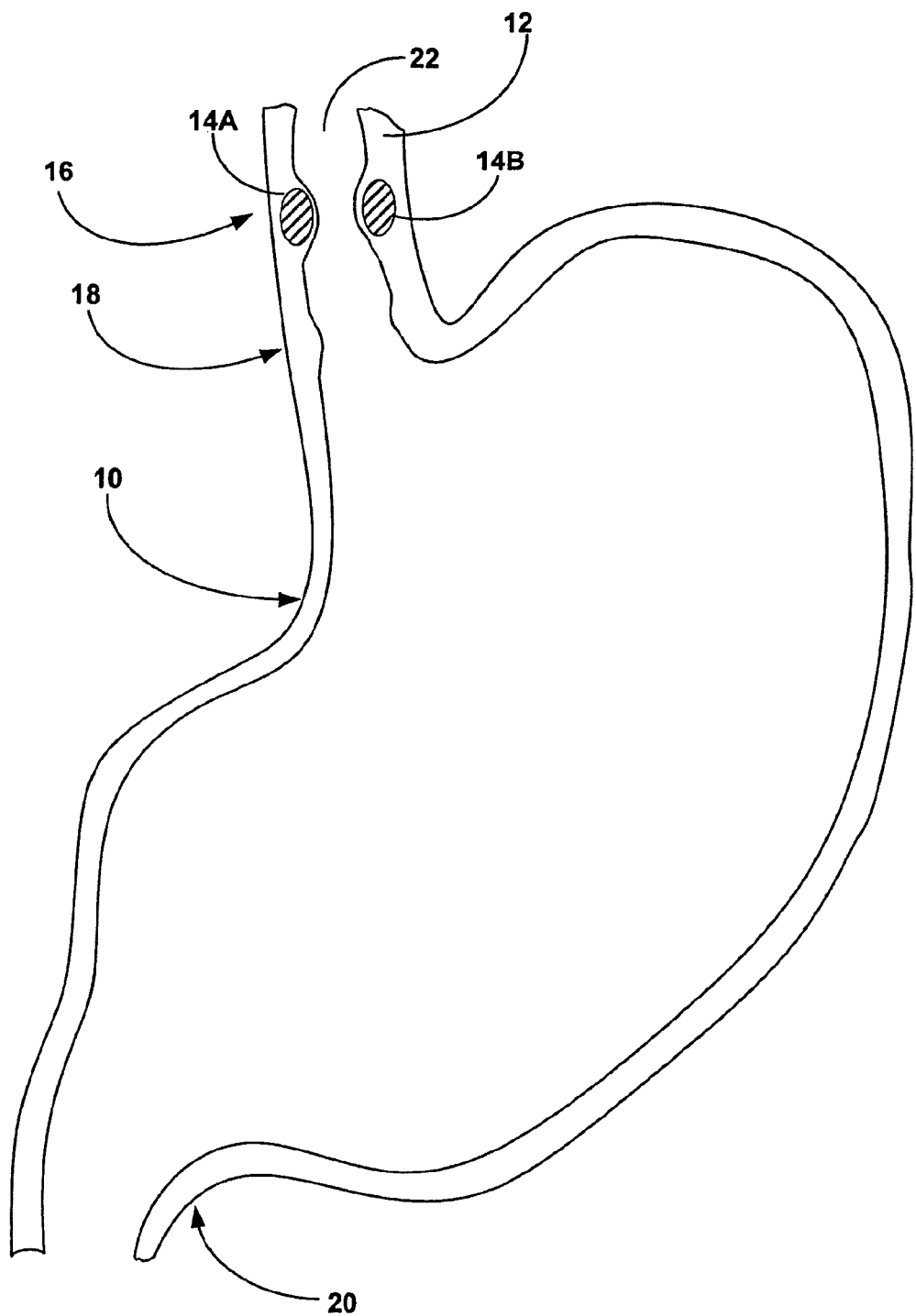
FIG. 9 depicts an esophagus with bulking devices implanted therein to form a partial obstruction in the esophagus

FIG. 9 is a cross-sectional diagram of the interior of a stomach 10 and esophagus 12 with implanted bulking devices 14A, 14B (hereinafter bulking devices 14) to form a partial obstruction 16 of the esophagus, in accordance with the invention. As shown in FIG. 1, esophagus 12 extends downward to join stomach 10 at lower esophageal sphincter (LES) 18, which regulates input to the stomach. Pyloric sphincter 20 joins stomach and the small intestine, and regulates output of stomach 10. Bulking devices 14 are implanted in a mucosal wall of esophagus 12 to reduce the diameter of an inner lumen 22 of the esophagus at a localized point and thereby form partial obstruction 16. Although FIG. 1 illustrates two bulking devices 14 in cross-section, additional bulking devices may be implanted at partial obstruction 16 at different angular positions about the circumference of esophagus 12.

In the example of FIG. 9, bulking devices 14 have a substantially elliptical capsule-like shape. In other embodiments, bulking devices 14 may have a variety of shapes, e.g., substantially spherically shaped, rod- or cylinder-shaped, or irregularly shaped. In an at least partially dehydrated state for implantation, an elliptical capsule-shaped bulking device 14 may have a minor axis width of approximately 2 mm, and a major axis length of approximately 20 mm. Following implantation in mucosal wall 37, the capsule-shaped bulking device 14 may have a minor axis width of approximately 6 mm and a major axis length of approximately 15 mm. This corresponds to an exemplary pre-implantation volume of less than approximately 65 mm$^3$ and a post-implantation volume of greater than or equal to approximately 400 mm$^3$.

Hence, in general, in an at least partially dehydrated state for implantation, each bulking device 14 may have a volume of less than approximately 100 mm$^3$. Upon expansion following implantation and subsequent rehydration, bulking device 14 may have a volume of greater than approximately 200 mm$^3$. In some embodiments, each bulking device 14 may have a pre-implantation volume of less than or equal to approximately 75 mm³ and a post-implantation volume of greater than or equal to approximately 300 mm³.

Hence, the bulking material may have an expansion ratio of greater than or equal to approximately 100 percent, or greater than or equal to approximately two times the pre-implantation size. In some embodiments, however, each bulking device 14 may have a larger volumetric expansion ratio, from an at least partially dehydrated state (pre-implantation) to a hydrated, expanded state (post-implantation), of at least approximately 4.5:1, and more particularly approximately 27:1. Other sizes and expansion ratios may be selected in accordance with the structural requirements for formation of a partial obstruction and the thickness of the esophageal wall in a given patient.

Bulking devices 14 may be placed at a series of regularly or irregularly spaced angular positions about the circumference of inner lumen 22 of esophagus 12. In some embodiments, two, three, four or more bulking devices 14 may be placed in esophagus 12. Spacing between adjacent bulking devices 14 may be controlled by taking into account the expanded size of the bulking devices. Adjacent bulking devices 20 may be separated about the circumference of inner lumen 22 by a section of intact mucosal tissue within the wall of esophagus 12. By leaving a substantial portion of the mucosal tissue intact, bulking devices 14 can contribute to partial obstruction 16 without substantially compromising the physiological function of esophagus in the digestion process.

Figure 10:
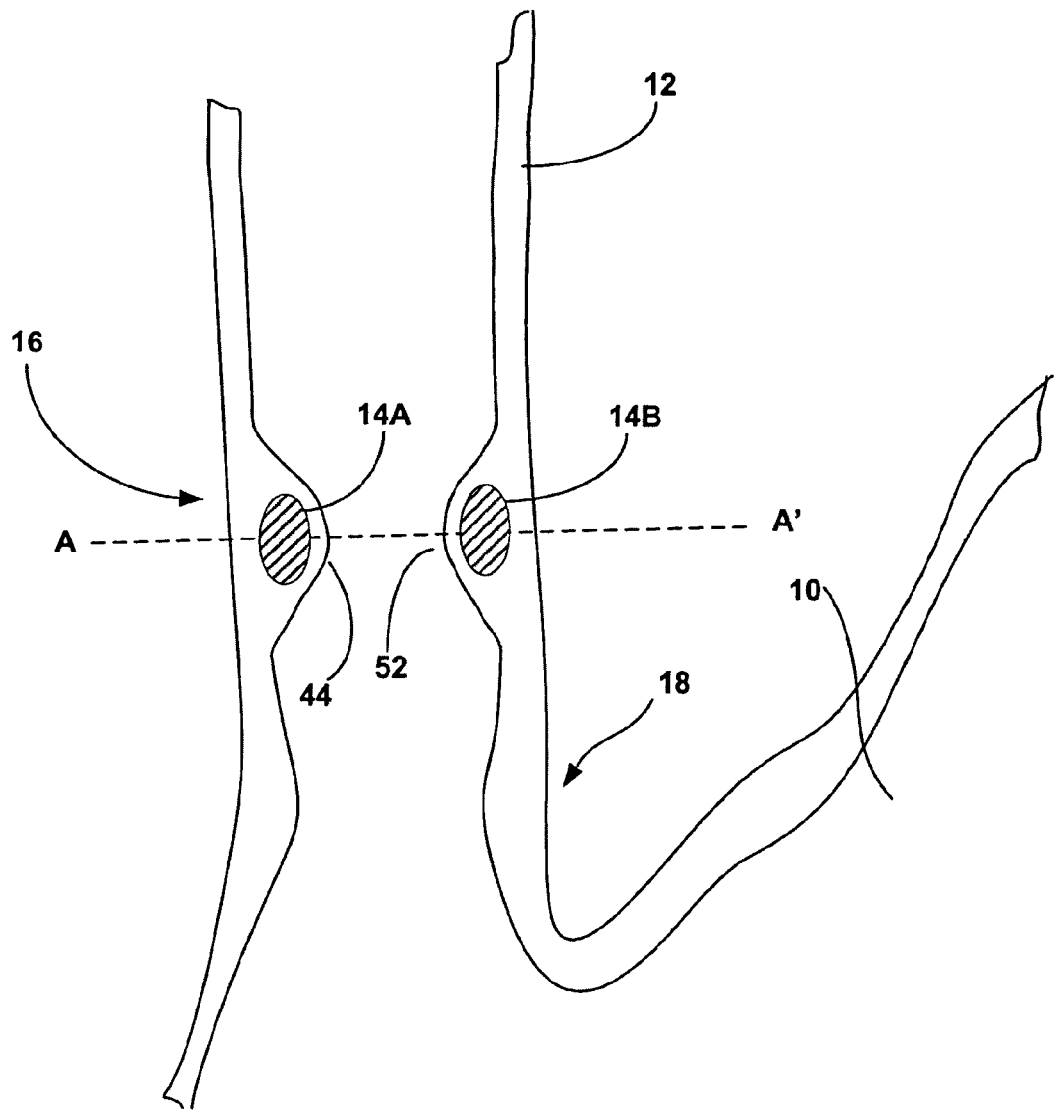
FIG. 10 is an enlarged view of a portion of the esophagus in the vicinity of the LES with bulking devices of the invention implanted therein.

FIG. 10 is an enlarged view of a portion of the esophagus 12 in the vicinity of the LES 18, illustrating expansion of bulking devices 14 following implantation to produce a partial obstruction 16 in the esophagus. In FIG. 10, bulking devices 14 are shown following implantation in an expanded state. As discussed above, bulking devices 14 may be formed from a variety of expandable materials that permit implantation of the bulking devices in an initial, reduced size, followed by post-implant expansion to form partial obstruction 16 of esophagus 12.

As an example, bulking devices 14 may be formed from a hydrogel material that is implanted in an at least partially dehydrated state. In a dehydrated state, the hydrogel materials is reduced in size. Following implantation within mucosal wall 37, bulking device 14 takes on moisture and rehydrates. In this manner, bulking device 14 expands to an enlarged size that further increases the size of partial obstruction 16.

Partial obstruction 16 is formed within esophagus 12 at any desired position between LES 18 and the upper esophageal sphincter (UES) (not shown) of the patient. The length of the esophagus varies from patient to patient, but is on the order or approximately 25 cm. As one example, partial obstruction 16 may be formed approximately midway between LES and the UES, e.g., approximately 8 to 16 cm above the LES. In other embodiments, it is sufficient that partial obstruction 16 be formed a short distance above the LES, e.g., greater than or equal to approximately 2 cm above the LES. In either case, partial obstruction 16 is not placed extremely close to either LES or UES, and therefore is less likely to alter or impair the function of either LES or UES. In other embodiments, however, a physician may elect to place partial obstruction 16 more closely to LES 18 or the UES.

Figure 11:
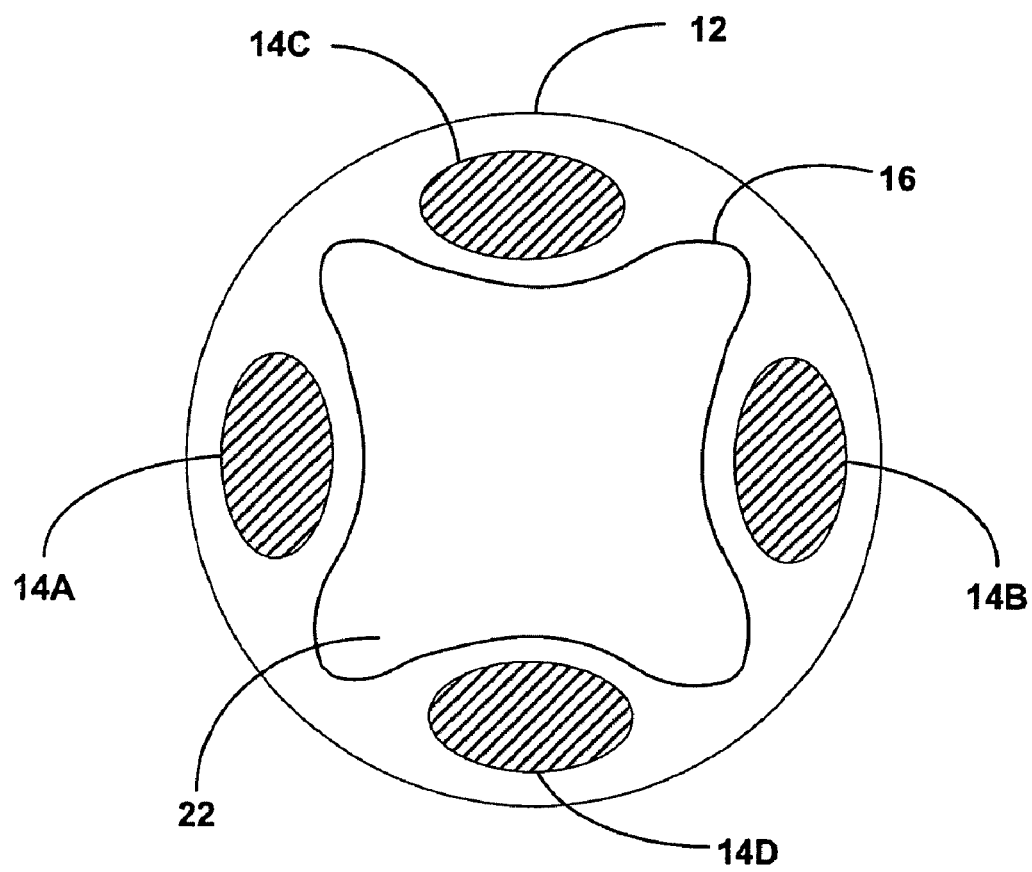
FIG. 11 is a cross sectional view of the portion of the LES depicted in FIG. 10 taken at the A-A line.

FIG. 11 is a cross-sectional end view of the esophagus 12 taken across line A-A' of FIG. 10, illustrating formation of a partial esophageal obstruction by a plurality of implanted bulking devices 14A, 14B visible in FIG. 10 and additional bulking devices 14C, 14D. In the example of FIG. 11, individual bulking devices 14A-14D are implanted at angular positions spaced approximately 90 degrees apart from one another around esophagus 12. In this manner, bulking devices 14A-14D combine to produce a partial obstruction 16 of the inner lumen 22 of esophagus 12. The number of bulking devices 14 implanted in esophagus 12 may vary, and may be more or less than the number of bulking devices shown in the example of FIG. 11.

Bulking devices of the invention can also be implanted within lumens of the urinary tract. The patient benefits by being enable to voluntarily control containment and release of urine. In the absence of a bulking device a physical deficit may be causing the patient to experience urinary incontinence. The deficit may be caused by old age, disease, trauma or another cause. In women, pregnancy can lead to urinary incontinence. Although the patient retains some control over the external urethral sphincter, the patient is unable to control containment and release of urine in a reliable manner. In some patients, urinary incontinence may be a problem when stressful events, such as sneezing, laughing, coughing, lifting, or other physical activity, puts pressure on the bladder. Women are especially vulnerable to stress-related urinary incontinence. With a bulking device(s) implanted outside the urethra, proximate to the external urinary sphincter, the patient has more bulk proximate to the urethra, and is therefore able to exercise voluntary control over the external urethral sphincter in order to close the urethra.

Figure 12:
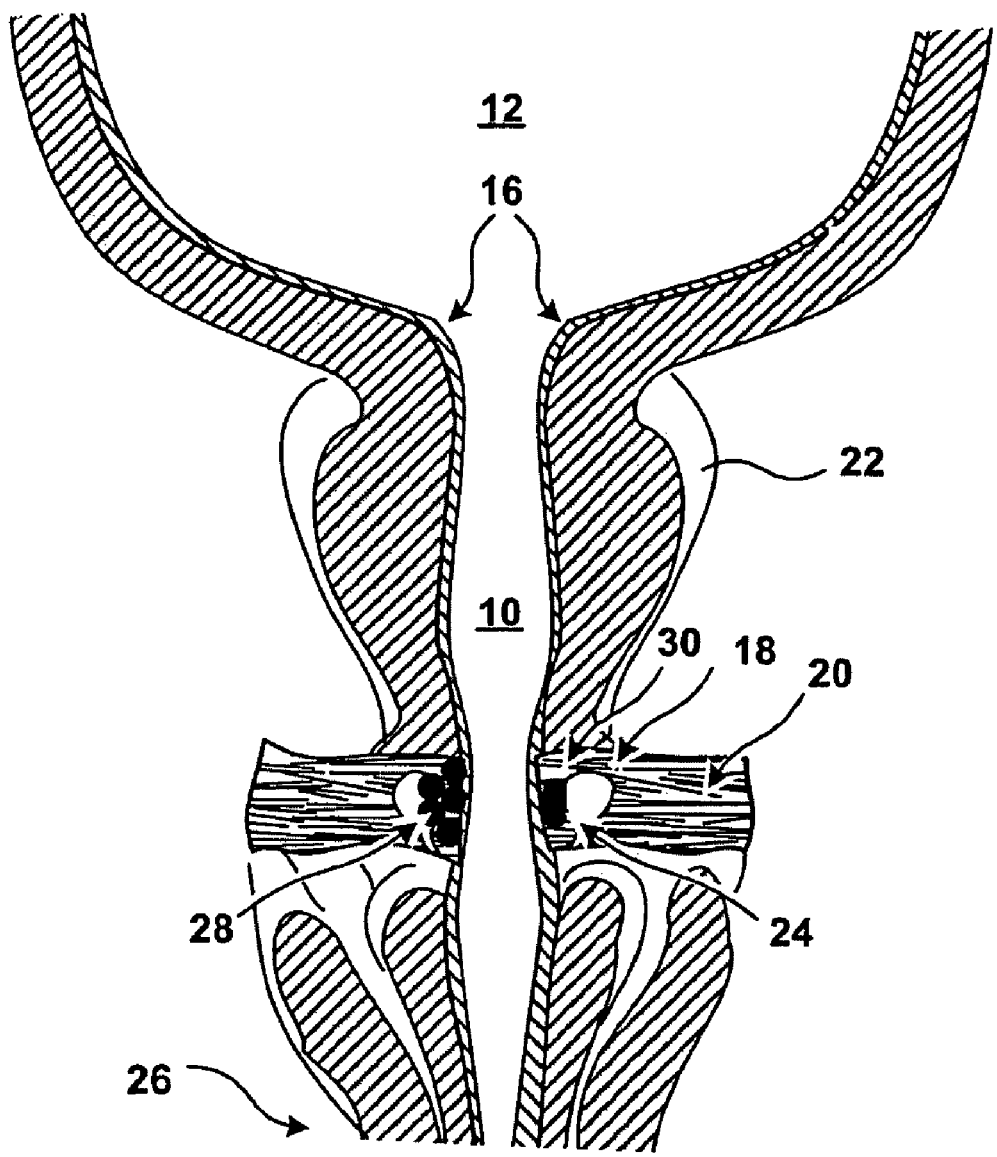
FIG. 12 is a cross section of a male urethra with two exemplary bulking devices implanted therein.

FIG. 12 is a coronal cross section of anatomical structures surrounding a urethra 10 of a male patient. Urethra 10 is a tube, including a wall and a lumen, that extends from the urinary bladder 12 to an external urethral orifice (not shown in FIG. 12). Flow of urine from bladder 12 and through urethra 14 is controlled by an internal urinary sphincter 16 and an external urinary sphincter 18. Internal urinary sphincter 16 is not really a separate muscle, but is a portion of bladder 12 that operates as a sphincter. Internal urinary sphincter 16 is not under voluntary control of the patient.

External urinary sphincter 18 is further away from bladder 12 than internal urinary sphincter 16. External urinary sphincter 18 encircles urethra 10 and is reinforced by the pelvic diaphragm 20. Contraction and relaxation of external urinary sphincter 18 is under the voluntary control of the patient.

These properties of the external urinary sphincter are true in women as well as in men, but in men, the prostate 22 encircling urethra 10 is interposed between bladder 12 and pelvic diaphragm 20. In addition, men have bulbourethral glands 24 proximate to pelvic diaphragm 20, and women do not. Furthermore, a man's urethra is typically much longer than a woman's urethra, because the urethra of a man traverses the penis 26.

FIG. 12 shows two of many possible deployments of bulking devices implanted proximate to external urinary sphincter 18. A bulking device in accordance with this embodiment includes a plurality of spherical units implanted in a region of tissue outside urethra 10 and proximate to external urinary sphincter 18. Another embodiment of a bulking device comprises a single capsule-shaped or substantially cylindrical device implanted in a region of tissue outside urethra 10 and proximate to external urinary sphincter 18. Although FIG. 12 shows deployment of both spherical devices and capsule-shaped devices, a physician may prefer to implant a device of a single configuration.

A bulking device may be any number of shapes, in addition to the capsule shape and multiple spherical shapes described above. Other shapes for a bulking device for implantation within the urinary tract, for example will be described below.

Figure 13:
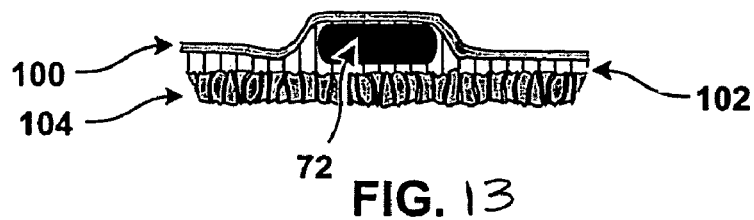
FIG. 13 depicts an exemplary bulking device of the invention.

A capsule-shaped bulking device, such as bulking device 72 shown in FIG. 13, or a or substantially cylindrical bulking device, may have a diameter of two to ten millimeters when in the enlarged state. In a typical application, the diameter of the bulking device may be two to four millimeters. The length of the bulking device may be four to twenty millimeters in the enlarged state, with a length of ten to fifteen millimeters being typical.

Figure 14:
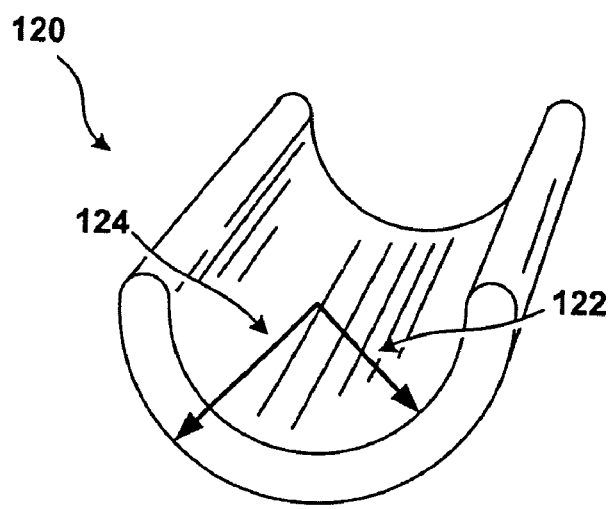
FIG. 14 depicts another exemplary bulking device of the invention.
Figure 15:
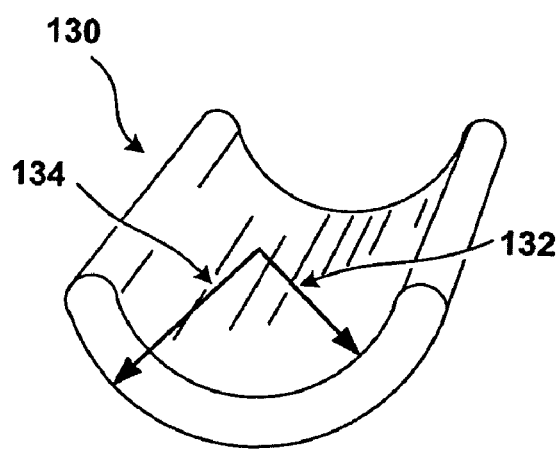
FIG. 15 depicts yet another exemplary bulking device of the invention.

FIGS. 14 and 15 illustrate two other exemplary bulking devices 120, 130. Bulking devices 120, 130 are shown in the enlarged state, and both are in the shape of a partial cylinder. Bulking device 120 shown in FIG. 14 is substantially a half-cylinder, and has a Cshaped or "horseshoe" shaped cross-section. Bulking device 120 has an inner surface radius 112 that is sized to conform to close the urethra of the patient when the patient exercises voluntary control over the external urethral sphincter. Inner surface radius 122 is sized to the dimensions of the urethra of a particular patient, with a typical inner surface radius 122 being in the range of one-half to fifteen millimeters. The outer surface radius 124 of bulking device 120 is larger than inner surface radius 122 by about one-half to five millimeters. The length of bulking device 120 may range from two to twenty millimeters. The cross-section of bulking device 120 need not be uniform, and bulking device 20 may resemble a curved wedge.

In one embodiment, two half-cylinder bulking devices like bulking device 120 may be implanted in a patient on opposite sides of the urethra. The two devices would not be coupled to one another, but their inner surfaces would be coaxial with the urethra of the patient. When the patient exercises voluntary control over the external urethral sphincter, the bulking devices supply the bulk to close the urethra. When the patient needs to urinate, however, the patient can relax the external urethral sphincter and allow the bulking devices to separate from one another, allowing the urethra to open and urine to pass.

Bulking device 130 shown in FIG. 15 is a partial cylinder, and is less than a half cylinder. Like bulking device 120, bulking device 130 has a C-shaped cross-section and an inner surface radius 132 that is sized to conform to close the urethra of the patient when the patient exercises voluntary control over the external urethral sphincter. In a typical implementation, inner surface radius 132 may be in the range of one-half to fifteen millimeters, and the outer surface radius 134 of bulking device 130 may be larger than inner surface radius 132 by about one-half to five millimeters. The length of bulking device 100 may range from two to twenty millimeters.

In one embodiment, three or four bulking devices like bulking device 130 may be implanted in a patient around the urethra. The inner surfaces of the devices would be coaxial with the urethra of the patient. When the patient exercises voluntary control over the external urethral sphincter, the bulking devices supply the bulk to close the urethra. When the patient needs to urinate, however, the patient can relax the external urethral sphincter and allow the bulking devices to separate from one another, allowing the urethra to open and urine to pass.

Bulking devices 120 and 130 in FIGS. 14 and 15, when in a miniature state, need not be C-shaped. Rather, the bulking device may be curled or folded to slide inside a needle, a catheter, or a sheathe.

In one embodiment where the bulking device is to be implanted in some portion of the urinary tract, the therapeutic substance can include an anti-infective agent, an anti-inflammatory agent, or some combination thereof. In one embodiment, a device of the invention for implantation into the urinary tract includes at least one of each of an anti-infective agent, and an anti-inflammatory agent. Embodiments for implantation into the urethra can also include one or more anti-cancer agents. Examples of anti-inflammatory agents can include, but are not limited to aspirin, salsalate, choline magnesium trisalicylate, etodolac, and indomethacin. In one embodiment of the invention, antibiotic agents can include, but are not limited to, penicillin, cefoxitin, oxacillin, tobramycin, gentamicin, ciprofloxacin, minocycline, rifampin. Examples of anti-cancer agents include, but are not limited to darbepoetin, irinotecan, cyclophosphamide, oxaliplatin, gemcitabine, imatinib, trastuzumab, gefitinib, chlorambucil, dronabinol, gemtuzumab, pegfilgrastim, epoetin alfa, methotrexate, bortezomib, and leucovorin.

In another embodiment of the invention, a bulking device can be implanted to treat fecal incontinence. A patient benefits from a bulking device(s) by being enable to voluntarily control containment and release of feces. In the absence of bulking devices, a physical deficit causes the patient to experience fecal incontinence. The deficit may be caused by old age, disease, trauma or other cause. Although the patient retains some control over his external anal sphincter, he is unable to control containment and release of feces. With bulking devices implanted in the anal walls, the patient has more bulk proximate to the anal opening, and is therefore able to exercise voluntary control over his external anal sphincter to close the anal opening.

Figure 16:
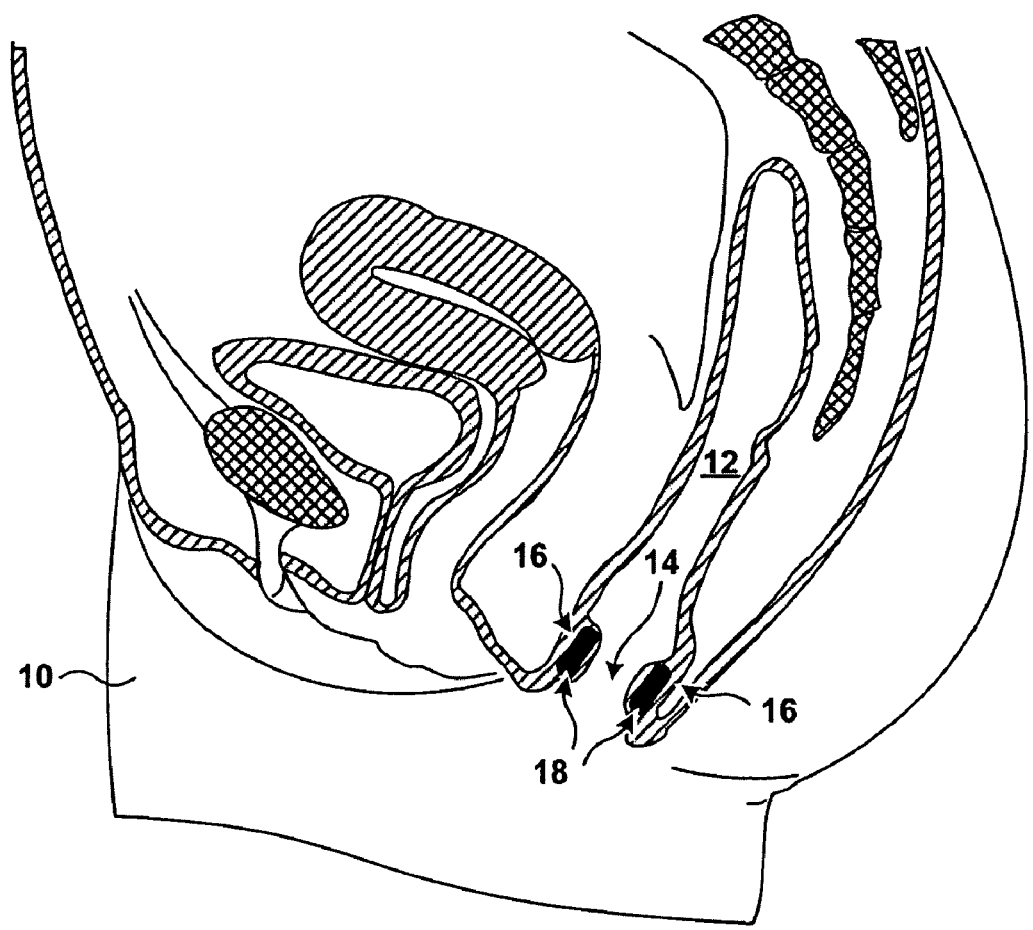
FIG. 16 depicts the pelvic region of a female patient with exemplary bulking devices of the invention implanted therein.

FIG. 16 is a sagittal cross section of a pelvic region of a female patient 10. In FIG. 16, the rectum 12 of patient 10 extends inferiorly and terminates with the anal opening or anal canal 14. The anal walls 16 proximate to anal opening 14 include a mucosa (not shown in FIG. 16) proximate to anal opening 14, a submucosa (not shown in FIG. 16) beneath the mucosa, and a musculature underlying the submucosa. The underlying musculature includes an internal anal sphincter (not shown in FIG. 16) and external anal sphincter (not shown in FIG. 16). The external anal sphincter, which is under the voluntary control of patient 10, is located more distally from anal opening 14 than is the internal anal sphincter.

FIG. 16 further shows bulking devices 18 implanted in the tissue of anal walls 16. Bulking devices 18 have been inserted in the tissue proximate to an anal sphincter. In the specific implantation shown in FIG. 16, bulking devices 18 have been implanted in the submucosa between the internal anal sphincter and the mucosa. In other implantations, bulking devices 18 may be implanted in or proximate to the musculature.

A bulking device may be any number of shapes, such as capsule-shaped (i.e., shaped substantially like a medicine capsule or a grain of rice) or spherical. Other shapes for a bulking prostheses will be described below.

Bulking devices for implantation into the anal sphincter can be similar in configuration as those for implantation in the urinary tract discussed above with respect to FIGS. 13, 14, and 15.

A capsule-shaped bulking device, such as the bulking device shown in FIG. 13, or a substantially cylindrical bulking device, may have a diameter of two to twenty millimeters when in the enlarged state. In a typical application, the diameter of the bulking device may be four to ten millimeters. The length of the bulking device may be four to forty millimeters in the enlarged state, with a length of ten to twenty millimeters being typical. To provide sufficient bulking, it may be beneficial to implant a plurality of such bulking devices. A typical patient may receive two to eight bulking devices arrayed proximate to an anal sphincter, with four to six perhaps being more typical.

Bulking devices for implantation in the vicinity of and around the vicinity of the anal sphincter may assume other shapes as well. A spherical bulking device, for example, may have a diameter of 0.2 millimeters to ten millimeters in the enlarged state, with a diameter of four to six millimeters being typical. A bulking device may also be for example, egg-shaped, with dimensions comparable to that of a spherical or capsule shaped bulking device. A typical patient may receive a plurality of bulking devices, with two to twenty bulking devices arrayed proximate to an anal sphincter.

With respect to FIG. 14, bulking devices that are substantially a half-cylinder, or have a Cshaped or "horseshoe" shaped cross-section can have an inner surface radius that is sized to conform to close the anus of the patient when the patient exercises voluntary control over the external sphincter. The inner surface radius is sized to the dimensions of the anus of a particular patient, with a typical inner surface radius being in the range of six to twenty-five millimeters. The outer surface radius of another embodiment of a bulking device is larger than inner surface radius by about two to ten millimeters. The length of bulking device may range from ten to forty millimeters. The cross-section of bulking device need not be uniform, and bulking device may resemble a curved wedge.

In a typical implantation, two half-cylinder bulking devices may be implanted in a patient on opposite sides of the anus. The two devices would not be coupled to one another, but their inner surfaces would be coaxial with the anus of the patient. When the patient exercises voluntary control over the external sphincter, the bulking devices supply the bulk to close the anus. When the patient needs to defecate, however, the patient can relax the external sphincter and allow the bulking devices to separate from one another, allowing the anus to open and waste to pass.

With respect to FIG. 15, a bulking device for implantation in the vicinity of or around the vicinity of an anal sphincter that are partial cylinder shaped, and are less than a half cylinder can have a C-shaped cross-section and an inner surface radius that is sized to conform to close the anus of the patient when the patient exercises voluntary control over the external sphincter. In a typical implementation, the inner surface radius may be in the range of six to twenty-five millimeters, and the outer surface radius of the bulking device may be larger than the inner surface radius by about two to ten millimeters. The length of bulking device may range from ten to forty millimeters.

In a typical implantation, three or four bulking devices like the bulking device discussed above may be implanted in a patient around the anus. The inner surfaces of the devices would be coaxial with the anus of the patient. When the patient exercises voluntary control over the external sphincter, the bulking devices supply the bulk to close the anus. When the patient needs to defecate, however, the patient can relax the external sphincter and allow the bulking devices to separate from one another, allowing the anus to open and waste to pass.

The bulking devices discussed above, when in a miniature state, need not be C-shaped. Rather, the devices may be curled or folded to slide inside a needle, a catheter, or a sheathe.

Figure 17:
FIG. 17 depicts another exemplary configuration of a bulking device of the invention.

FIG. 17 is a side view of a bulking device 110, in a miniature state. Bulking device 110 can be made from a hydrogel material in the inert state, that is, bulking device 110 is formed from a hydrophilic polymer that forms a hydrogel in the presence of water. Bulking device 110 is substantially rod-like. Bulking device 110 in FIG. 17 is similar in construction and dimension to capsule-shaped bulking devices described above, but includes a sharpened tip 112. Tip 112 is sufficiently sharp to allow tip 112 to penetrate the tissues of a patient.

In one embodiment where the bulking device is to be implanted in the vicinity of or around the fecal sphincter, the therapeutic substance can include an anti-infective agent, an anti-inflammatory agent, or some combination thereof. In one embodiment, a device of the invention for implantation in the vicinity of or around the fecal sphincter includes at least one of each of an anti-infective agent, and an anti-inflammatory agent. Examples of anti-inflammatory agents can include, but are not limited to aspirin, salsalate, choline magnesium trisalicylate, etodolac, and indomethacin. In one embodiment of the invention, antibiotic agents can include, but are not limited to, penicillin, cefoxitin, oxacillin, tobramycin, gentamicin, ciprofloxacin, minocycline, rifampin.

Thus, embodiments of devices for augmenting a lumen wall are disclosed. One skilled in the art will appreciate that the present invention can be practiced with embodiments other than those disclosed. The disclosed embodiments are presented for purposes of illustration and not limitation.

What is claimed is:

1. A bulking device for implantation into a gastrointestinal tract of a patient, for the treatment of obesity comprising:
   a bulking material that is configured to alter a portion of the gastrointestinal tract into which it is implanted; and
   a plurality of therapeutic agents effective in combination to treat obesity in association with the bulking material;
   wherein the bulking material is a swellable material, a hydrogel and a partially hydrolyzed polyacrylonitrile.

2. The device of claim 1, wherein the partially hydrolyzed polyacrylonitrile is a hydrophilic polyacrylonitrile copolymer.

3. A bulking device for implantation into a gastrointestinal tract of a patient, for the treatment of obesity comprising:
   a bulking material that is configured to alter a portion of the gastrointestinal tract into which it is implanted; and
   a plurality of therapeutic agents effective in combination to treat obesity in association with the bulking material;
   wherein at least one of the plurality of therapeutic agents decreases the absorption of one or more specific nutrients.

4. The device of claim 3, wherein the specific nutrient is lipids.

5. The device of claim 4, wherein the at least one of the plurality of therapeutic agents is orlistat.

6. A bulking device for implantation into a gastrointestinal tract of a patient, for the treatment of obesity comprising:
   a bulking material that is configured to alter a portion of the gastrointestinal tract into which it is implanted; and
   a plurality of therapeutic agents effective in combination to treat obesity in association with the bulking material;
   wherein at least one of the plurality of therapeutic agents is a motility enhancer.

7. The device of claim 6,
   wherein the motility enhancer comprises at least one of cholinergic receptor agonist, a motilin receptor agonist, and a dopamine receptor antagonists.

8. A bulking device for implantation into a gastrointestinal tract of a patient, for the treatment of obesity comprising:
   a bulking material that is configured to alter a portion of the gastrointestinal tract into which it is implanted; and
   a plurality of therapeutic agents effective in combination to treat obesity in association with the bulking material;
   wherein at least one of the plurality of therapeutic agents is an anti-inflammatory agent and wherein at least one of the plurality of therapeutic agents is an anti-infective agent.

9. The device of claim 8, wherein the anti-inflammatory agent comprises at least one of aspirin, salsalate, choline magnesium trisalicylate, etodolac, and indomethacin.

10. The device of claim 8, wherein the anti-infective agent comprises at least one of penicillin, cefoxitin, oxacillin, tobramycin, gentamicin, ciprofloxacin, minocycline, and rifampin.

* * * * *